(12) United States Patent
Duke et al.

(10) Patent No.: US 11,406,296 B2
(45) Date of Patent: Aug. 9, 2022

(54) SYSTEM AND METHOD FOR ASSESSING RISK ASSOCIATED WITH A GLUCOSE STATE

(71) Applicant: Roche Diabetes Care, Inc., Indianapolis, IN (US)

(72) Inventors: David L. Duke, Fishers, IN (US); Abhishek S. Soni, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 299 days.

(21) Appl. No.: 16/576,561

(22) Filed: Sep. 19, 2019

(65) Prior Publication Data
US 2020/0008723 A1 Jan. 9, 2020

Related U.S. Application Data

(62) Division of application No. 13/645,198, filed on Oct. 4, 2012, now Pat. No. 10,463,282.

(51) Int. Cl.
| | |
|---|---|
| *A61B 5/145* | (2006.01) |
| *G16H 50/30* | (2018.01) |
| *G16H 50/20* | (2018.01) |
| *A61B 5/00* | (2006.01) |

(52) U.S. Cl.
CPC ........ *A61B 5/14532* (2013.01); *A61B 5/7275* (2013.01); *G16H 50/20* (2018.01); *G16H 50/30* (2018.01)

(58) Field of Classification Search
None
See application file for complete search history.

(56) References Cited

U.S. PATENT DOCUMENTS

| | | |
|---|---|---|
| 6,615,064 B1 | 9/2003 | Aldrich |
| 9,247,901 B2 | 2/2016 | Kamath et al. |
| 10,463,282 B2 | 11/2019 | Duke et al. |

(Continued)

FOREIGN PATENT DOCUMENTS

| | | |
|---|---|---|
| CN | 1422136 A | 6/2003 |
| CN | 100448392 C | 1/2009 |

(Continued)

OTHER PUBLICATIONS

Palerm et al. Hypoglycemia detection and prediction using continuous glucose monitoring—A study on hypoglycemic clamp data, 2007, Diabetes Technology Society, 624-629 (Year: 2007).*

(Continued)

*Primary Examiner* — Michael R Bloch
(74) *Attorney, Agent, or Firm* — Faegre Drinker Biddle & Reath LLP

(57) ABSTRACT

A system and method is provided for analyzing a glucose state. A method may include identifying a target glucose state and an initial glucose state. The method may include calculating a target return path for a transition from the initial glucose state to the target glucose state. The target return path may comprise at least one intermediate glucose state associated with the transition from the initial glucose state to the target glucose state. The target return path may be calculated based on a hazard associated with the at least one intermediate glucose state of the target return path.

19 Claims, 18 Drawing Sheets

(56) References Cited

U.S. PATENT DOCUMENTS

| | | | |
|---|---|---|---|
| 2002/0132279 | A1 | 9/2002 | Hockersmith |
| 2003/0212317 | A1 | 11/2003 | Kovatchev et al. |
| 2003/0235817 | A1* | 12/2003 | Bartkowiak ....... A61B 5/14532 |
| | | | 435/5 |
| 2005/0203360 | A1 | 9/2005 | Brauker et al. |
| 2007/0168145 | A1* | 7/2007 | Beyer ................. C12Q 1/006 |
| | | | 702/85 |
| 2008/0154513 | A1 | 6/2008 | Kovatchev et al. |
| 2009/0164239 | A1* | 6/2009 | Hayter ................. H04W 4/80 |
| | | | 705/2 |
| 2010/0298685 | A1* | 11/2010 | Hayter ................. A61M 5/142 |
| | | | 600/365 |

FOREIGN PATENT DOCUMENTS

| | | |
|---|---|---|
| CN | 102770761 A | 11/2012 |
| JP | 2003-079723 A | 3/2003 |
| JP | 2005-520662 A | 7/2005 |
| JP | 2007-014751 A | 1/2007 |
| WO | 01/13786 A1 | 3/2001 |
| WO | 2010/135638 A2 | 11/2010 |

OTHER PUBLICATIONS

Cameron, Fraser, et al. "A Closed Loop Artificial Pancreas Based on Risk Management", Journal of Diabetes Science and Technology: vol. 5, issue 2, Mar. 2011, pp. 368-379.

Clarke, et al., "Statistical Tools to Analyze Continuous Glucose Monitor Data", Diabetes Technology & Therapeutics, vol. 11, Suppl. 1, 2009; p. S-45-S-54.

Cobelli, et al., "Diabetes: Models, Signals, and Control", IEEE Reviews in Biomedical Engineering, vol. 2, 2009; p. 54-96.

Examination Report dated Mar. 14, 2017, issued by the Japanese Patent Office for related Application No. 2015-534976; 6 pages.

Examination report issued by the European Patent Office, Munich, dated Jan. 10, 2019, for related Application No. EP13777248.9; 9 pages.

Guerra, Stefania, et al. "A Dynamic Risk Measure from Continuous Glucose Monitoring Data", Diabetes Technology & Therapeutics, vol. 13, No. 8, 2011, pp. 843-853.

International Preliminary Reporton Patentability received for PCT Patent Application No. PCT/EP2013/070412, dated Apr. 16, 2015, 9 pages.

International Search Report and Written Opinion received for PCT Patent Application No. PCT/EP2013/070412, dated Sep. 15, 2014, 11 pages.

Kovatchev, Boris, et al. "Symmetrization of the Blood Glucose Measurement Scale and Its Applications", Diabetes Care: vol. 20, No. 11, Nov. 1997, pp. 1655-1658.

Palerm, CC,et al, "Hypoglycemia Detection and Prediction Using Continuous Glucose Monitoring—A Study on Hypoglycemic Clamp Data", Journal of Diabetes Science and Technology (Online). 2007;1(5):624-629.

State Intellectual Property Office of People's Republic China; First Office Action dated Apr. 5, 2016; Application No. 201380052129.0.

\* cited by examiner

|  | idx→ | 1 | 2 | 3 | 4 | 5-797 | 798 | 799 |
|---|---|---|---|---|---|---|---|---|
| idx↓ | ΔBG↓,BG→ | 1.0 | 1.5 | 2.0 | 2.5 | ... | 399.5 | 400 |
| 401 | 5 | | | | | | | |
| 400 | 4.975 | | | | | | | |
| ⋮ | ⋮ | | | | | | | |
| 2 | -4.975 | | | | | | | |
| 1 | -5 | | | | | | | |

SYSTEM AND METHOD FOR ASSESSING RISK ASSOCIATED WITH A GLUCOSE STATE

RELATED APPLICATIONS

The present application is a divisional of, and claims the benefit of, U.S. patent application Ser. No. 13/645,198, filed Oct. 4, 2012, now U.S. Pat. No. 10,463,282, issued Nov. 5, 2019 and titled "SYSTEM AND METHOD FOR ASSESSING RISK ASSOCIATED WITH A GLUCOSE STATE," the entire disclosure of which is hereby incorporated herein by reference in its entirety.

TECHNICAL FIELD

The present disclosure relates generally to continuous blood glucose monitoring (CGM) and in particular to systems and methods for assessing risk associated with a glucose state.

BACKGROUND

Biological monitoring provides health care providers (HCPs) and patients with biological data that can be utilized to treat and/or manage a medical condition related to the biological data. For example, continuous glucose monitoring (CGM) devices provide glucose data related to a detected level or concentration of glucose contained within the blood of people with diabetes (PwDs). Hazard metrics may be derived from glucose data for assessing a hazard to the diabetic person based on a detected glucose level. However, current hazard metrics often fail to account for the rate of change of the glucose data and the uncertainty of the accuracy of the glucose data. As such, current hazard metrics are often not appropriate to use as a metric for optimizing therapy or for evaluating the total amount of risk over a window of CGM measurements.

For example, a known hazard metric includes the hazard function illustrated in graph 10 of FIG. 1 and proposed in the following paper: Kovatchev, B. P. et al., *Symmetrization of the blood glucose measurement scale and its applications*, Diabetes Care, 1997, 20, 1655-1658. The Kovatchev hazard function of FIG. 1 is defined by the equation h(g)=[1.509 (log(g)$^{1.0804}$−5.381)]$^2$, wherein g is the blood glucose concentration (in milligrams per deciliter or mg/dl) shown on the x-axis and h(g) is the corresponding penalty value shown on the y-axis. The Kovatchev function provides a static penalty (i.e., hazard) value in that the penalty depends only on the glucose level. The minimum (zero) hazard occurs at 112.5 mg/dl, as shown at region 12 of FIG. 1. The hazard with the glucose level approaching hypoglycemia (region 14) rises significantly faster than the hazard with the glucose level approaching hyperglycemia (region 16).

The Kovatchev hazard function fails to account for the rate of change of the glucose level as well as the uncertainty associated with the measured glucose level. For example, a patient's hazard associated with 100 mg/dl and a rapidly falling blood glucose level is likely greater than the patient's hazard associated with 100 mg/dl with a constant glucose rate of change. Further, measured glucose results from a glucose sensor may contain sensor noise, such as noise due to physical movement of the glucose sensor relative to the person's body or due to electrical noise inherent in the glucose sensor. Further, the glucose sensor may malfunction, such as due to electronics or battery failure or due to detachment or dropout of the sensor. As such, the measured glucose level may not be accurate. The penalty values provided with the Kovatchev function fail to account for such uncertainty in the measured glucose level.

Accordingly, some embodiments of the present disclosure provide risk metrics associated with measured CGM data that account for the blood glucose level, the rate of change of the blood glucose level, and/or the uncertainty associated with the blood glucose level and the rate of change. Further, some embodiments of the present disclosure calculate a target return path from a given glucose state to a target glucose state based on one or more risk or hazard metrics associated with intermediate glucose states of the target return path.

SUMMARY

In an exemplary embodiment of the present disclosure, a method of analyzing a glucose state is provided. The method includes identifying, by at least one computing device, a target glucose state including a target glucose level and a target rate of change of the target glucose level. The method includes identifying, by the at least one computing device, an initial glucose state including an initial glucose level and an initial rate of change of the initial glucose level. The initial glucose state is different from the target glucose state. The method further includes calculating, by hazard analysis logic of the at least one computing device, a target return path for a transition from the initial glucose state to the target glucose state. The target return path includes at least one intermediate glucose state associated with the transition from the initial glucose state to the target glucose state. The target return path is calculated by the hazard analysis logic based on a hazard associated with the at least one intermediate glucose state of the target return path.

In another exemplary embodiment of the present disclosure, a method of analyzing a glucose state of a person with diabetes is provided. The method includes detecting, by at least one computing device, a glucose state of the person based on at least one measured glucose value provided with a glucose sensor. The detected glucose state includes a glucose level of the person and a rate of change of the glucose level. The method further includes determining, by hazard analysis logic of the at least one computing device, a target return path for a transition from the detected glucose state to a target glucose state. The target glucose state includes a target glucose level and a target rate of change of the target glucose level. The target return path includes at least one intermediate glucose state associated with the transition from the detected glucose state to the target glucose state. The method further includes computing, by the hazard analysis logic of the at least one computing device, at least one risk metric associated with the detected glucose state based on the at least one intermediate glucose state of the target return path.

In yet another exemplary embodiment of the present disclosure, a non-transitory computer-readable medium is provided. The non-transitory computer-readable medium includes executable instructions such that when executed by at least one processor cause the at least one processor to identify a target glucose state including a target glucose level and a target rate of change of the target glucose level. The executable instructions further cause the at least one processor to identify an initial glucose state including an initial glucose level and an initial rate of change of the initial glucose level. The initial glucose state is different from the target glucose state. The executable instructions further cause the at least one processor to calculate a target return path for a transition from the initial glucose state to the target glucose state. The target return path includes at least one intermediate glucose state associated with the transition from the initial glucose state to the target glucose state. The target return path is calculated by the at least one processor based on a hazard associated with the at least one intermediate glucose state of the target return path.

In still another exemplary embodiment of the present disclosure, a non-transitory computer-readable medium is provided. The non-transitory computer-readable medium includes executable instructions such that when executed by at least one processor cause the at least one processor to detect a glucose state of the person based on at least one measured glucose value provided with a glucose sensor. The detected glucose state includes a glucose level of the person and a rate of change of the glucose level. The executable instructions further cause the at least one processor to determine a target return path for a transition from the detected glucose state to a target glucose state. The target glucose state includes a target glucose level and a target rate of change of the target glucose level. The target return path includes at least one intermediate glucose state associated with the transition from the detected glucose state to the target glucose state. The executable instructions further cause the at least one processor to compute at least one risk metric associated with the detected glucose state based on the at least one intermediate glucose state of the target return path.

BRIEF DESCRIPTION OF THE DRAWINGS

The features and advantages of the present invention will become more apparent to those skilled in the art upon consideration of the following detailed description taken in conjunction with the accompanying figures, wherein

FIG. 6 illustrates an exemplary penalty matrix populated by the method of FIGS. 4 and 5 that may function as a lookup table for a given glucose state;

DETAILED DESCRIPTION

Figure 1:
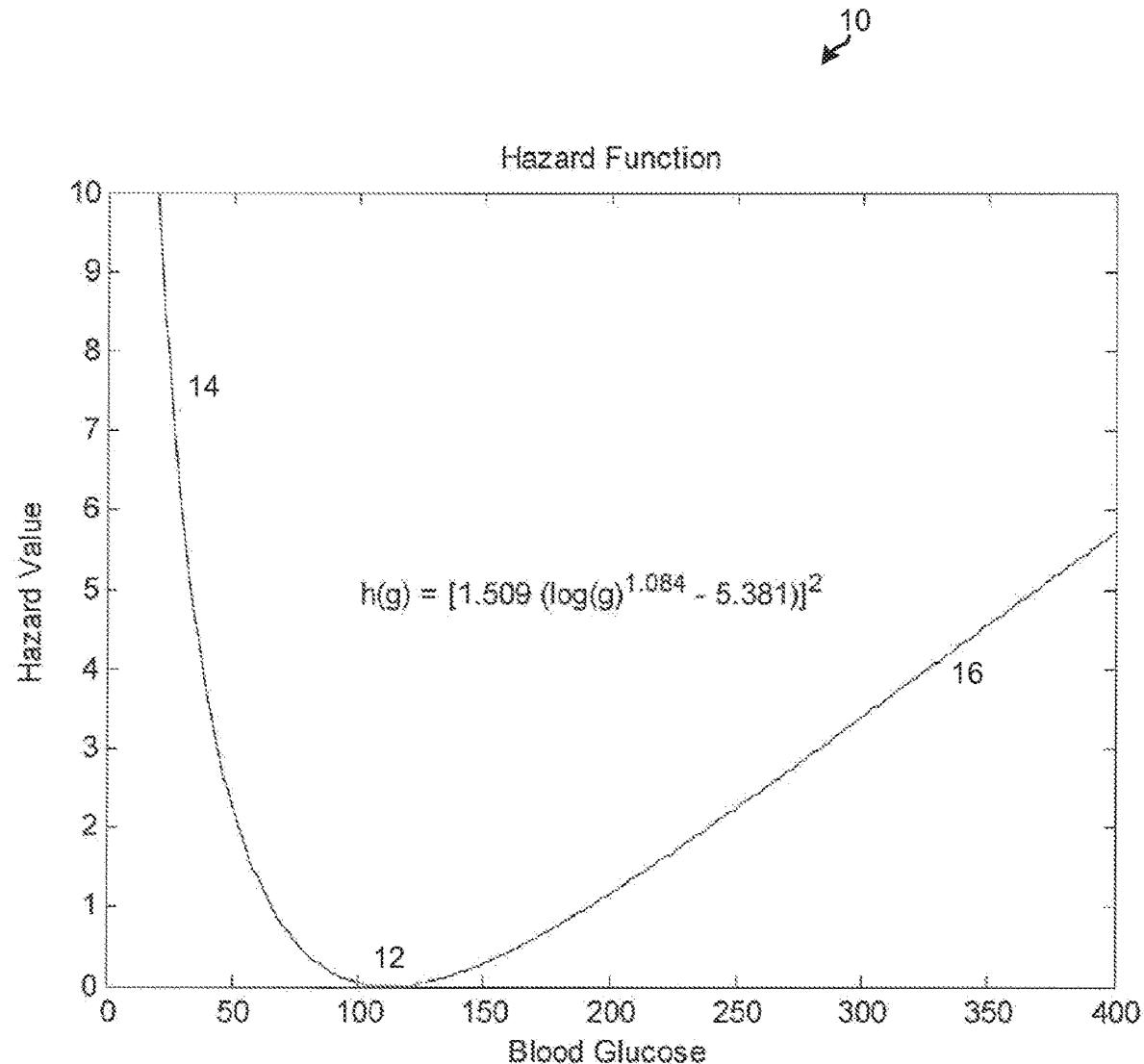
FIG. 1 illustrates a known hazard function for assessing the hazard associated with a glucose level.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The term "logic" or "control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

As used herein, the "measured glucose values" or "measured glucose results" are the glucose levels of the person as measured by a glucose sensor; the "actual glucose level" is the actual glucose level of the person; and the "estimated glucose level" is the estimated glucose level of the person, which may be based on the measured glucose values.

Figure 1A:
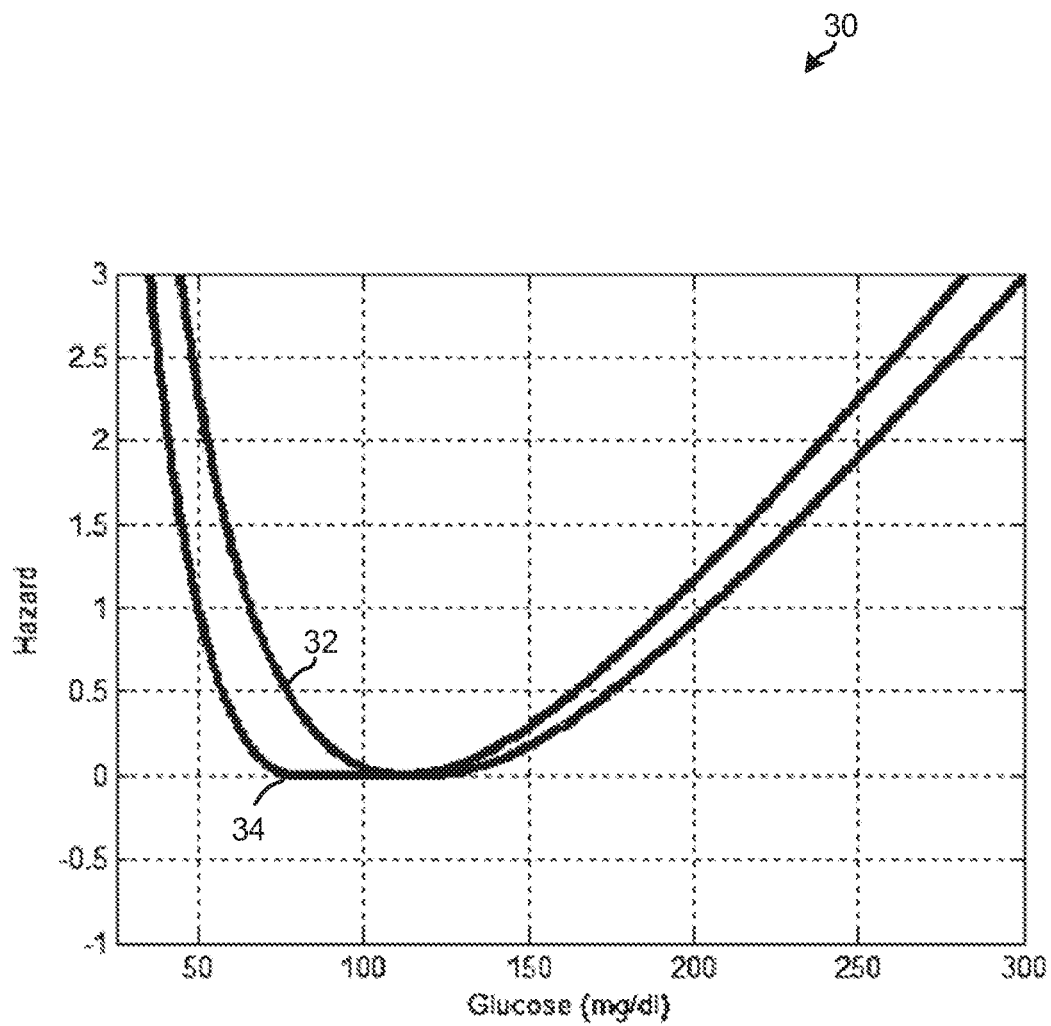
FIG. 1A illustrates another exemplary hazard function for assessing the hazard associated with a glucose level.

FIG. 1A illustrates another exemplary hazard function 30 for calculating static penalty values for a given glucose level. The hazard function 30 is defined by the following equation:

$$h(g) = \begin{cases} 0, & g_1 \leq g \leq g_2 \\ \alpha(\log(g)^c - \log(g_2)^c), & g_2 < g \\ \alpha\left(\log(g)\frac{\log(\beta)}{\log(\log(g_1))} - \beta\right), & g_1 > g \end{cases} \quad (1)$$

wherein g is the blood glucose level (mg/dl) shown on the x-axis, h(g) is the corresponding static penalty value shown on the y-axis, and $g_1$ and $g_2$ are glucose levels used to define a range of target glucose values ($g_1 \leq g \leq g_2$) or a single target glucose value ($g_1 = g_2$). In the illustrated embodiment, the variables α, β, and c are defined as follows: α=1.509, β=5.381, and c=1.084. The range of target glucose values ($g_1 \leq g \leq g_2$) illustratively has a corresponding penalty value of zero, as shown with equation (1). With the target glucose level $g_1=g_2=112.5$ mg/dl, hazard function 30 generates the hazard curve 32 of FIG. 1A, which corresponds to the Kovatchev function. With $g_1=75$ mg/dl and $g_2=125$ mg/dl, the hazard function 30 generates the hazard curve 34 of FIG. 1A. As such, hazard curve 34 provides penalty values for a given glucose state when the target glucose range is defined from 75 mg/dl to 125 mg/dl. Other suitable target glucose levels/ranges and penalty values corresponding to the target glucose levels/ranges may be provided.

Figure 2:
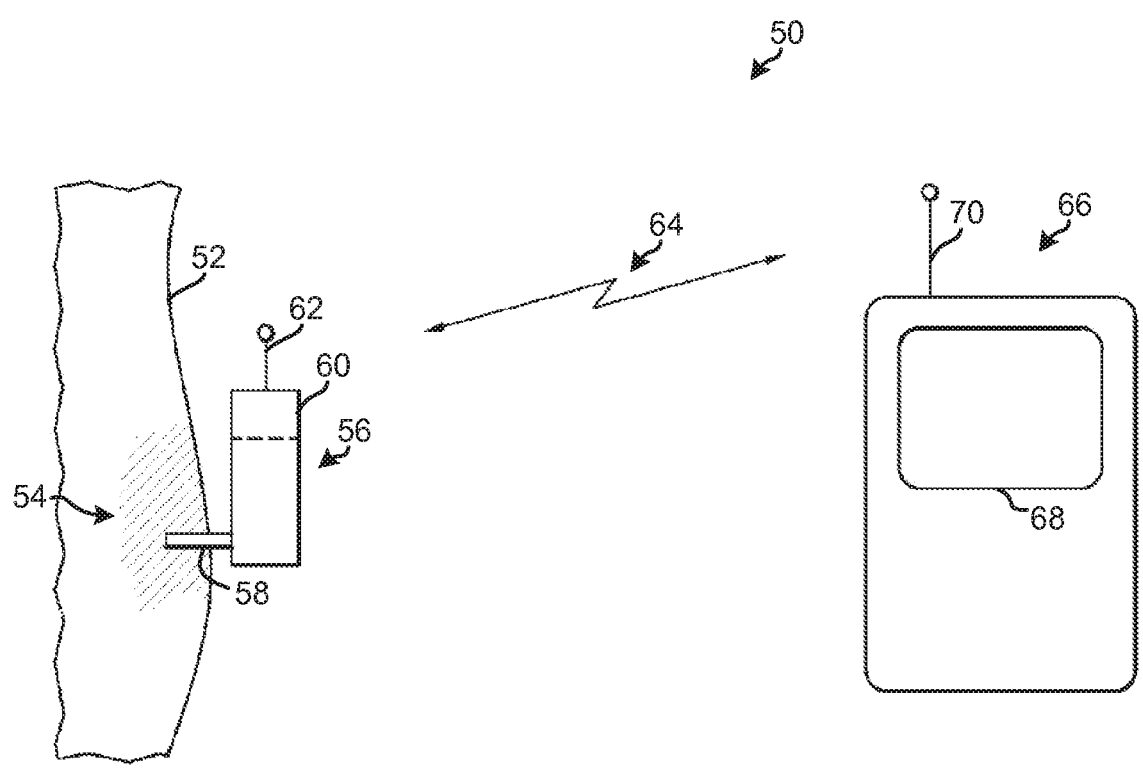
FIG. 2 illustrates a continuous glucose monitoring (CGM) system according to one or more embodiments described herein.

Referring to FIG. 2, an exemplary continuous glucose monitoring (CGM) system 50 is illustrated for monitoring the glucose level of a person having diabetes. In particular, CGM system 50 is operative to collect a measured glucose value at a predetermined, adjustable interval, such as every one minute, five minutes, or at other suitable intervals. CGM system 50 illustratively includes a glucose sensor 56 having a needle or probe 58 that is inserted under the skin 52 of the person. The end of the needle 58 is positioned in interstitial fluid 54, such as blood or another bodily fluid, such that measurements taken by glucose sensor 56 are based on the level of glucose in interstitial fluid 54. Glucose sensor 56 is positioned adjacent the abdomen of the person or at another suitable location. In one embodiment, glucose sensor 56 is periodically calibrated in order to improve its accuracy. This periodic calibration may help correct for sensor drift due to sensor degradation and changes in the physiological condition of the sensor insertion site. Glucose sensor 56 may comprise other components as well, including but not limited to a wireless transmitter 60 and an antenna 62. Although glucose sensor 56 illustratively uses a needle 58 to gain access to the person's blood or other fluid, glucose sensor 56 may use other suitable devices for taking measurements, such as, for example, a non-invasive device (e.g., infrared light sensor).

Upon taking a measurement, glucose sensor 56 transmits the measured glucose value via a communication link 64 to a computing device 66, illustratively a glucose monitor 66. Communication link 64 is illustratively wireless, such as radio frequency ("RF") or other suitable wireless frequency, in which the measured glucose results are transmitted via electromagnetic waves. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association.® (IrDA.®). Other suitable types of wireless communication may be provided. Communication link 64 may be unidirectional (i.e., data is transmitted only from glucose sensor 56 to computing device 66) or bidirectional (i.e., data is transmitted between glucose sensor 56 and computing device 66 in either direction). Furthermore, communication link 64 may facilitate communication between two or more devices, such as between glucose sensor 56, computing device 66, a therapy device (e.g., insulin pump), and other suitable devices or systems. Although FIG. 2 illustrates a wireless communication link 64, a wired link may alternatively be provided, such as, for example, a wired Ethernet link. Other suitable public or proprietary wired or wireless links may be used.

Figure 3:
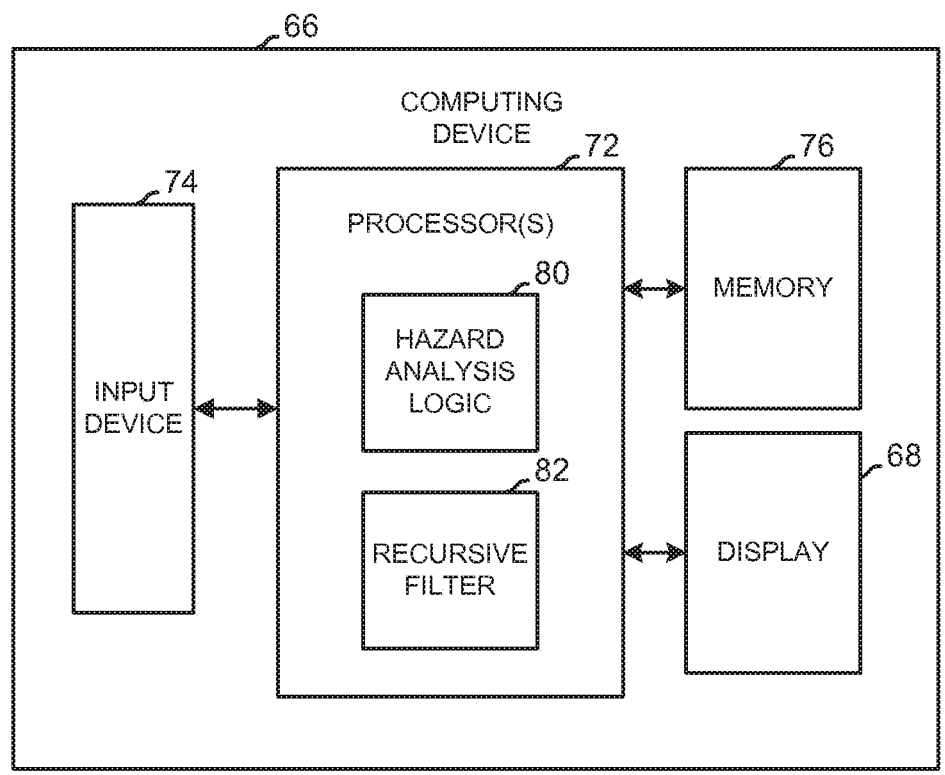
FIG. 3 illustrates an exemplary computing device of the CGM system of FIG. 2 including hazard analysis logic.

FIG. 3 illustrates an exemplary computing device 66 of the CGM system 50 of FIG. 2. Computing device 66 includes at least one processor 72 that executes software and/or firmware code stored in memory 76 of computing device 66. The software/firmware code contains instructions that, when executed by the processor 72 of computing device 66, causes computing device 66 to perform the functions described herein. Computing device 66 may alternatively include one or more application-specific integrated circuits (ASICs), field-programmable gate arrays (FPGAs), digital signal processors (DSPs), hardwired logic, or combinations thereof. While computing device 66 is illustratively a glucose monitor 66, other suitable computing devices 66 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although computing device 66 is illustrated as a single computing device 66, multiple computing devices may be used together to perform the functions of computing device 66 described herein.

Memory 76 is any suitable computer readable medium that is accessible by processor 72. Memory 76 may be a single storage device or multiple storage devices, may be located internally or externally to computing device 66, and may include both volatile and non-volatile media. Further, memory 76 may include one or both of removable and non-removable media. Exemplary memory 76 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by computing device 66.

Computing device 66 further includes an input device 74 electrically coupled to processor 72. Input device 74 includes any suitable wireless and/or wired communication module operative to communicate data over communication link 64 between processor 72 and glucose sensor 56. In one embodiment, input device 74 includes an antenna 70 (FIG. 2) for receiving and/or transmitting data wirelessly over communication link 64. In the illustrated embodiment, input device 74 is configured to receive data, such as measured glucose results from glucose sensor 56 of FIG. 2, and to provide the received data to processor 72. Computing device 66 stores in memory 76 measured glucose results received from glucose sensor 56 via input device 74.

Computing device 66 further includes a display 68 electrically coupled to processor 72. Display 68 may comprise any suitable display or monitor technology (e.g., liquid crystal display, etc.) configured to display information provided by processor 72 to a user. Processor 72 is configured to transmit to display 68 information related to the detected or estimated glucose state of the person. The displayed information may include the estimated glucose state of the person and/or a predicted glucose state of the person at some time in the future. The glucose state may include the estimated glucose level and/or the estimated rate-of-change of the glucose level. The displayed information may also include an estimate of the quality or uncertainty of the estimated glucose level. Moreover, the displayed information may include warnings, alerts, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 milligrams of glucose per deciliter of blood (mg/dl). Computing device 66 may also be configured to tactilely communicate information or warnings to the person, such as for example by vibrating.

In one embodiment, computing device 66 is in communication with a remote computing device, such as at a caregiver's facility or a location accessible by a caregiver, and data (e.g., glucose data or other physiological information) is transferred between them. In this embodiment, computing device 66 and the remote device are configured to transfer physiological information through a data connection such as, for example, via the Internet, cellular communications, or the physical transfer of a memory device such as a diskette, USB key, compact disc, or other portable memory device.

As described in greater detail herein, processor 72 of computing device 66 includes hazard analysis logic 80 operative to calculate a target return path from each of a plurality of given glucose states to a target glucose state. Cumulative penalty values associated with the target return paths are stored in a matrix that may be used as a lookup table, as described herein. The target glucose state is illustratively the optimal or ideal glucose state having no associated hazard, although any suitable target glucose state may be identified. Each target return path is comprised of a plurality of glucose states that are intermediate the given glucose state and the optimal glucose state. In the illustrated embodiment, each return path is calculated such that a total estimated hazard associated with the intermediate glucose states along the return path is minimized. Based on the calculated return path, various control strategies may be employed by computing device 66, such as adjustment of a therapy to the person, for example. In addition, hazard control logic 80 calculates a plurality of risk metrics associated with each given glucose state based on the calculated return path of the given glucose state. In the illustrated embodiment, hazard control logic 80 is further configured to analyze measured glucose results provided with glucose sensor 56 to determine a probability of accuracy of glucose sensor 56. Furthermore, computing device 66 includes a recursive filter 82 configured to estimate a glucose state of the person by weighting the measured glucose results with the probability of glucose sensor accuracy. Further, hazard analysis logic 80 is operative to calculate a risk associated with a detected glucose state based on a penalty value associated with the detected glucose state and based on the uncertainty of the detected glucose state, as described herein.

Figure 4:
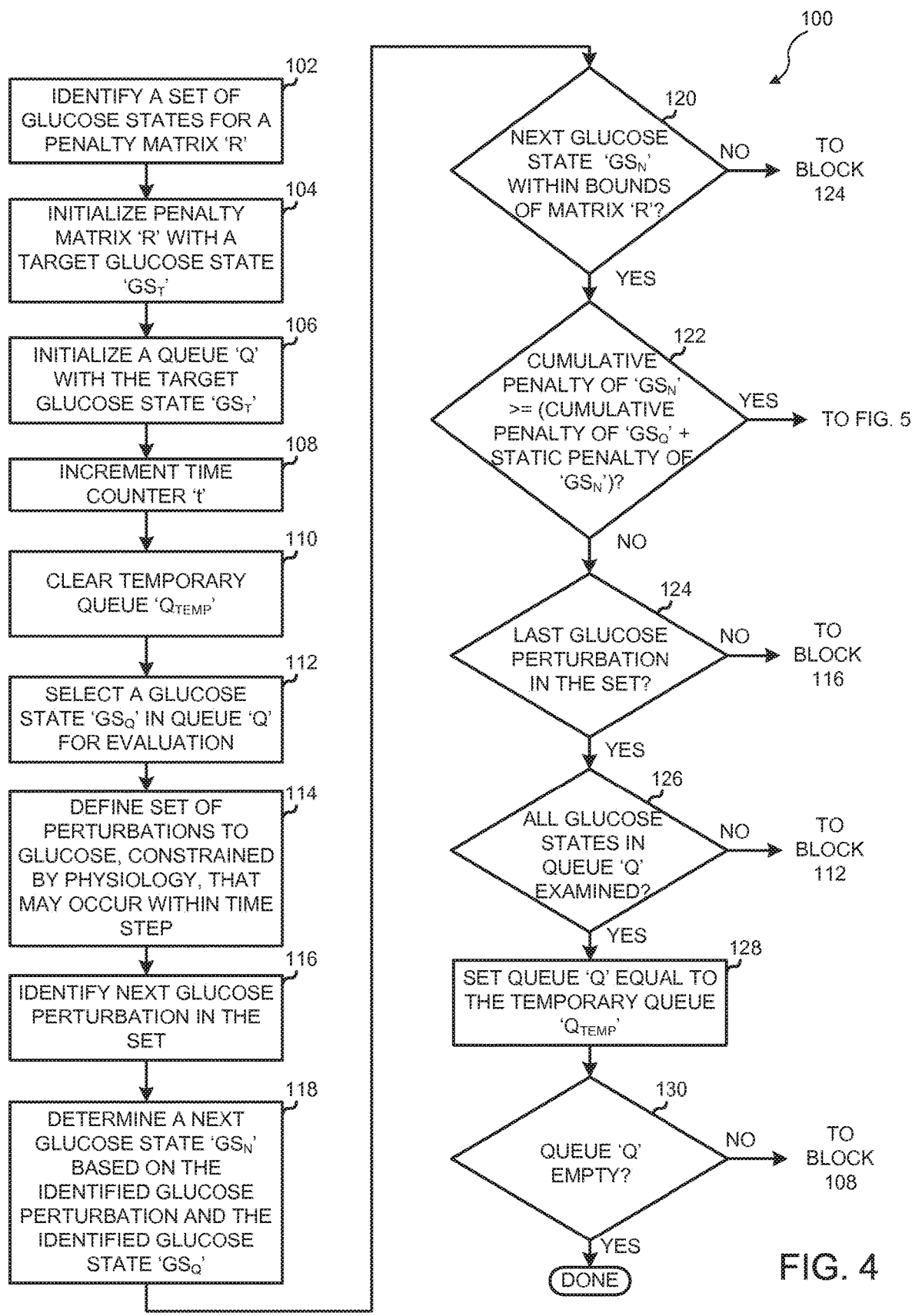
FIGS. 4 and 5 are a flow chart of an exemplary method of operation of the computing device of FIG. 3 for calculating a return path to a target glucose state from a plurality of glucose states based on at least one risk metric.
Figure 5:
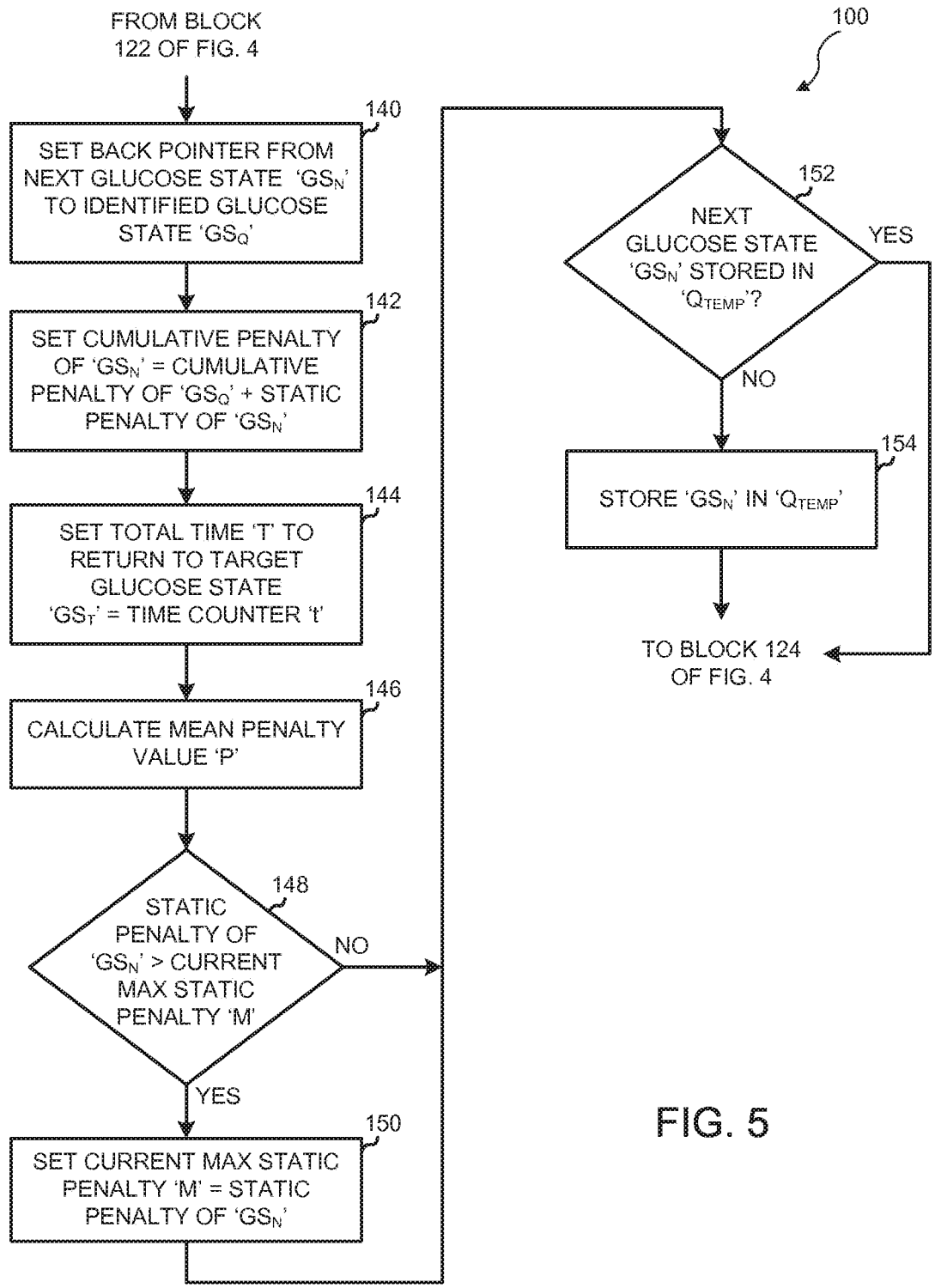

Referring to FIGS. 4 and 5, a flow diagram 100 of an exemplary iterative method performed by hazard analysis logic 80 of processor 72 is illustrated for calculating a return path to a target glucose state for each of a plurality of glucose states based on at least one hazard metric. In the illustrated embodiment, logic 80 calculates the target return path for each glucose state by populating a penalty matrix wherein each cell or block of the penalty matrix represents a different glucose state. As described herein, each glucose state represented by the cells of the matrix includes a glucose level and a rate of change of the glucose level. The target return path is comprised of a plurality of intermediate glucose states, each represented by a cell of the matrix. The penalty matrix contains a cumulative penalty value for each glucose state based on the total hazard encountered along the target return path from the respective glucose state, as described herein.

Referring to block 102 of FIG. 4, logic 80 first identifies a set of glucose states for a penalty matrix. In particular, the size, boundaries, and step-size of the penalty matrix are determined to identify the set of glucose states to be evaluated in the method. See, for example, exemplary penalty matrix R illustrated in FIG. 6. In matrix R of FIG. 6, each column represents a blood glucose level BG ranging from 1 mg/dl to 400 mg/dl with a step-size of 0.5 mg/dl. Each row of matrix R represents a rate of change of the glucose level ΔBG ranging from −5 mg/dl/min to 5 mg/dl/min (milligrams of glucose per deciliter of blood per minute) with a step-size of 0.025 mg/dl/min. As such, the resulting size of matrix R is 799 by 401 (a total of 320399 cells), with each cell representing a different glucose state, i.e., each cell representing a different combination of a blood glucose level BG and a glucose rate of change ΔBG. Other suitable boundaries and step-sizes of matrix R may be provided to identify fewer or additional glucose states. The rows and columns of matrix R are shown condensed in FIG. 6 for illustrative purposes. As described below, each cell of penalty matrix R is populated with a cumulative penalty value by the method of FIGS. 4 and 5.

In an exemplary embodiment, logic 80 further populates additional matrices by the method of FIGS. 4 and 5 that represent additional risk or hazard metrics for the set of glucose states defined for matrix R. The matrices include an estimated return time matrix T, a maximum penalty matrix M, and a mean penalty rate matrix P, and each matrix has the same size, boundaries, and step-size of penalty matrix R defined at block 102. In addition, logic 80 populates a back pointer matrix B corresponding to the size and boundaries of matrix R. Each cell of the back pointer matrix B is populated with a back pointer that points to another cell. As such, a target return path from a given glucose state to the target glucose state is identified based on the back pointer associated with each glucose state (i.e., each cell) of the target return path. Each cell of the return time matrix T is populated with an estimated total time for a person's blood glucose to transition from the glucose state of the corresponding cell to the target glucose state along the calculated target return path. Each cell of the maximum penalty matrix M is populated with maximum cumulative penalty value of all glucose states along the target return path from and including the glucose state of the corresponding cell to the target glucose state. Each cell of the mean penalty rate matrix P is populated with an estimated average penalty rate associated with the target return path calculated for the corresponding glucose state. In one embodiment, each matrix R, T, M, P, and B comprises data stored in memory 76 of computing device 66. As described herein, the values contained in matrices R, T, M, and P serve as risk metrics for detected and/or identified glucose states.

At block 104, logic 80 initializes the penalty matrix R with a target glucose state $GS_T$. In the illustrated embodiment, the target glucose state $GS_T$ is the optimal glucose state of 112.5 mg/dl with a rate of change of 0 mg/dl/min, as determined by the Kovatchev function described herein. The target glucose state $GS_T$ may include another suitable target glucose state or a range of glucose states. Logic 80 initializes the matrix R by setting the penalty value associated with the target glucose state $GS_T$ cell ($R_{112.50}$) to zero. In one embodiment, logic 80 further initializes matrices T, M, and P by setting respective time value, maximum penalty value, and mean penalty rate to zero for the target glucose state. In one embodiment, logic 80 further initializes all the other glucose states (cells) of the matrix R with a large value, such as 100,000 or another suitable large number.

At block 106, logic 80 initializes a queue Q that identifies cells to be evaluated. On a first iteration of the method, logic 80 adds the target glucose state $GS_T$ to the queue Q to initialize the queue Q. As such, following block 106, queue Q initially identifies a single cell to evaluate, i.e., the cell that corresponds to the target glucose state $GS_T$. At block 108, logic 80 increments a time counter t by a predetermined time step. In one embodiment, time counter t is initially zero, and logic 80 increments time counter by one minute at block 108. In one embodiment, the time step is set to a small value (e.g., one minute) such that the discrete steps analyzed by the method approximate a continuous system. Other suitable time increments may be implemented. At block 110, logic 80 clears a temporary queue $Q_{TEMP}$, which is used to store next glucose states $GS_N$ that are later added to queue Q for evaluation by the method, as described herein.

At block 112, logic 80 selects a glucose state $GS_Q$ from queue Q for evaluation. On the initial iteration of block 112, the selected glucose state $GS_Q$ is the target glucose state $GS_T$. On later iterations, queue Q includes additional glucose states available for selection at block 112 for evaluation, as described herein. With the glucose state of interest $GS_Q$ identified, logic 80 defines a set of perturbations to glucose that could occur within the time step, as represented with block 114. The perturbations are identified based on assumed physiological constraints associated with a blood glucose state. The set of perturbations are used to identify other potential glucose states that a person could transition to within the time step (e.g., one minute) from the glucose state of interest $GS_Q$. In other words, the extent of change to a person's blood glucose state within one minute (or other suitable time step) is limited naturally by physiological constraints. As such, logic 80 defines the set of perturbations based on at least one assumed maximum degree of perturbation that could occur within the time step. Based on the assumed maximum degree of perturbation, logic 80 identifies a set of perturbation values at block 114 that fall within a range defined by the maximum degree of perturbation.

In the exemplary embodiment, the perturbations defined at block 114 are acceleration values associated with a glucose level. In this example, logic 80 assumes a maximum acceleration threshold based on physiological constraints and, based on the assumed maximum acceleration and the glucose state of interest $GS_Q$, calculates several other potential glucose states that could be attained within the time step. An exemplary maximum acceleration threshold is ±0.025 mg/dl/min². As such, logic 80 defines a set of acceleration values at block 114 to range from −0.025 mg/dl/min² to +0.025 mg/dl/min². Logic 80 selects a plurality of discrete accelerations from the defined range to use as the set of acceleration values. An exemplary set of acceleration values is [−0.025, −0.020, −0.015, −0.010, −0.005, 0.000, +0.005, +0.010, +0.015, +0.020, +0.025] (mg/dl/min²).

The maximum acceleration may be adjusted to account for different metabolisms of the person with diabetes. In one embodiment, the maximum acceleration is set to substantially match the physiology of the patient. For example, a child's glucose levels may fluctuate more rapidly than an adult's glucose levels. As such, a higher maximum acceleration may be appropriate for persons with a higher metabolism (e.g., children) and a lower maximum acceleration for persons with a lower metabolism (e.g., adults). An exemplary high maximum acceleration threshold is ±0.025 mg/dl/min², and an exemplary low maximum acceleration threshold is ±0.020 mg/dl/min², although other suitable maximum accelerations may be used.

At block 116, logic 80 identifies or selects a perturbation value (e.g., acceleration value) from the defined set of perturbation values for evaluation. Based on the glucose state of interest $GS_Q$ and the perturbation value identified at block 116, logic 80 identifies a next glucose state $GS_N$ at block 118 that is to be evaluated by the method. For example, with acceleration as the exemplary perturbation, logic 80 determines the next glucose state $GS_N$, including a blood glucose level and an associated rate of change, based on the known glucose level and known rate of change of the selected glucose state $GS_Q$ and based on the acceleration value selected at block 116. For example, logic 80 calculates a glucose level $G_N$ and glucose rate of change $dG_N$ of the next glucose state $GS_N$ with the following equations:

$$G_N = G_Q - dG_Q*dt - 0.5*a*dt*dt \quad (2)$$

$$dG_N = dG_Q - a*dt \quad (3)$$

wherein $G_Q$ is the glucose level of the glucose state $GS_Q$, $dG_Q$ is the rate of change of the glucose state $GS_Q$, dt is the time step identified in block 108 (e.g., one minute), and a is the acceleration value identified at block 116. In one embodiment, logic 80 rounds off the calculated values for $G_N$ and $dG_N$ to the nearest step-size as defined by the cells of matrix R. For example, the blood glucose values of the cells of matrix R of FIG. 6 illustratively have a step size of 0.5 mg/dl and the rate of change have a step size of 0.025 mg/dl/min. At block 120, logic 80 determines if the next glucose state $GS_N$ as defined by the rounded values for $G_N$ and $dG_N$ falls within the bounds of matrix R, i.e., whether a cell of matrix R corresponds to the next glucose state $GS_N$.

If the next glucose state $GS_N$ is not in matrix R at block 120, logic 80 skips block 122 and proceeds to block 124. If the next glucose state $GS_N$ is in matrix R at block 120, logic 80 proceeds to block 122 to assess the hazard associated with the next glucose state $GS_N$. At block 122, logic 80 determines if the cumulative penalty value associated with the next glucose state $GS_N$ is greater than the sum of the cumulative penalty value of the glucose state of interest $GS_Q$ and the static penalty value of the next glucose state $GS_N$. In the illustrated embodiment, the static penalty value of a glucose state is provided by the Kovatchev function described herein. In another embodiment, the static penalty value of a glucose state is provided by the hazard function 30 described herein with respect to FIG. 1A. Other suitable hazard functions may be used. The cumulative penalty value of a given glucose state is the sum of the static penalty value of that given glucose state and the static penalty values of each intermediate glucose state identified by the method along the target return path associated with that glucose state. As such, the cumulative penalty value of the glucose state of interest $GS_Q$ is the sum of the static penalty value of $GS_Q$ and the static penalty values of all intermediate glucose states associated with the target return path calculated (by prior iterations of the method) for that glucose state $GS_Q$. For a first iteration of the method, $GS_Q$ is the optimal glucose state $GS_T$ and thus has a cumulative penalty value of zero. For later iterations, $GS_Q$ may be any other glucose state of the matrix R having an associated cumulative penalty value that was calculated by prior iterations of the method of FIGS. 4 and 5. Similarly, the cumulative penalty value of the next glucose state $GS_N$ is based on a prior calculated target return path that is associated with that state $GS_N$. Thus, if the next glucose state $GS_N$ was already evaluated on a prior iteration of the method, $GS_N$ will have an associated target return path and thus an associated cumulative penalty value. However, if the current iteration of the method is the first time the next glucose state $GS_N$ has been evaluated by the method, then the next glucose state $GS_N$ will not have an associated target return path yet. For the first iteration of the method, the cumulative penalty value of $GS_N$ is the static penalty value of $GS_N$.

Thus, logic 80 determines at block 122 if the cumulative penalty of the target return path previously calculated for the next glucose state $GS_N$ is greater than the cumulative penalty of the target return path currently being evaluated for $GS_N$, i.e., the cumulative penalty of the target return path for $GS_Q$ plus the static hazard value of $GS_N$. If yes, then logic 80 determines that a more optimal target return path (i.e., a path having a smaller cumulative penalty value) for $GS_N$ has been found. Thus, logic 80 assigns the new target return path for $GS_N$ to be the currently evaluated target return path for $GS_Q$ plus the transition step from $GS_N$ to $GS_Q$. In particular, with block 122 being true, the method proceeds to block 140 of FIG. 5 where logic 80 sets a back pointer from $GS_N$ to $GS_Q$ to thereby tie $GS_N$ to the target return path defined for $GS_Q$. Logic 80 sets the back pointer in the cell of matrix B corresponding to the next glucose state $GS_N$. At block 142, logic 80 sets the cumulative penalty value of $GS_N$ in the matrix R to be equal to the sum of the cumulative penalty value of $GS_Q$ and the static penalty value of $GS_N$. At block 144, logic 80 sets in matrix T a total estimated return time for $GS_N$ to be equal to the time counter t. As such, the total estimated return time set at block 144 is the estimated time to return to the target glucose state $GS_T$ from the next glucose state $GS_N$ along the new target return path set for $GS_N$ at block 140. The time counter t is incremented during the method for each evaluated glucose state along the target return path for $GS_N$. For example, if the target return path for $GS_N$ set at block 140 includes four intermediate glucose states between $GS_N$ and $GS_T$, then the time counter t will be equal to five (including the increment from $GS_Q$ to $GS_N$). Thus, in this example, the total return time calculated at block 144 would be equal to five minutes (based on a time step of one minute).

At block 146, logic 80 calculates the mean penalty rate associated with the target return path for $GS_N$. The mean penalty rate for $GS_N$ is calculated as the cumulative penalty value set at block 142 divided by the total time set at block 144. Logic 80 sets the calculated mean penalty rate in the cell of matrix P corresponding to the next glucose state $GS_N$. At block 148, logic 80 determines if the static penalty value of glucose state $GS_N$ is greater than the current maximum static penalty value associated with the target return path for $GS_N$. In particular, if the static penalty value of $GS_N$ is greater than the static penalty value of each intermediate glucose state along the target return path for $GS_N$, then logic 80 sets at block 150 the maximum static penalty value associated with the target return path for $GS_N$ to equal the static penalty value of $GS_N$. If block 148 is false, then logic 80 sets the current maximum penalty value associated with the target return path of $GS_Q$ to $GS_N$, i.e., logic 80 sets the maximum static penalty value in the cell of matrix M corresponding to $GS_N$.

At block 152, logic 80 determines if the next glucose state $GS_N$ is stored in the temporary queue $Q_{TEMP}$. If not, logic 80 stores the state $GS_N$ in $Q_{TEMP}$, and proceeds to block 124 of FIG. 4. If $GS_N$ is already stored in $Q_{TEMP}$ (i.e., if $GS_N$ has already been evaluated since clearing $Q_{TEMP}$ at block 110), the method proceeds to block 124. At block 124 of FIG. 4, logic 80 determines if the perturbation value (e.g., acceleration value) identified in block 116 was the last value of the set of perturbation values defined in block 114. If additional perturbation values in the set have not yet been evaluated, the method returns to block 116 to select another perturbation value from the set for evaluation with the glucose state $GS_Q$. The method then calculates a different next glucose state $GS_N$ at block 118 based on the new perturbation value and repeats blocks 120-124. Once all perturbation values of the set have been evaluated at block 124, logic 80 proceeds to block 126 to determine if all glucose states identified by queue Q have been evaluated. If additional glucose states in queue Q have not been evaluated, the method returns to block 112 to select another glucose state of interest $GS_Q$ from queue Q for evaluation. Logic 80 then repeats blocks 114-124 for each glucose state of queue Q. Once all glucose states in queue Q have been evaluated at block 126, logic 80 clears queue Q and sets queue Q equal to $Q_{TEMP}$ at block 128, i.e., all glucose states that were added to $Q_{TEMP}$ (at block 154 of FIG. 5) are placed in queue Q. As such, if queue Q is not empty at block 130, logic 80 returns to block 108 and evaluates all of the glucose states that were placed in queue Q at block 128. Once the queue Q is empty at block 130, which indicates that none of the next glucose states $GS_N$ evaluated on the last iteration of the method were within the bounds of matrix R at block 120 or that no new optimal return paths were found for any of the next glucose states $GS_N$, then the method is complete.

In one embodiment, the method completes with all matrices R, T, M, P, and B being fully populated. If one or more cells of matrix R are left unpopulated following completion of the method, the cumulative penalty value for these corresponding glucose states may be set equal to the largest penalty value contained in the matrix R with an identical+/− sign (i.e., hypo or hyper hazard). In another embodiment, the unpopulated glucose states (cells) of matrix R may be set to a value greater than the largest penalty value. In another embodiment, the unpopulated glucose states (cells) of matrix R may be identified as failsafe states that lead to an alert.

Figure 7:
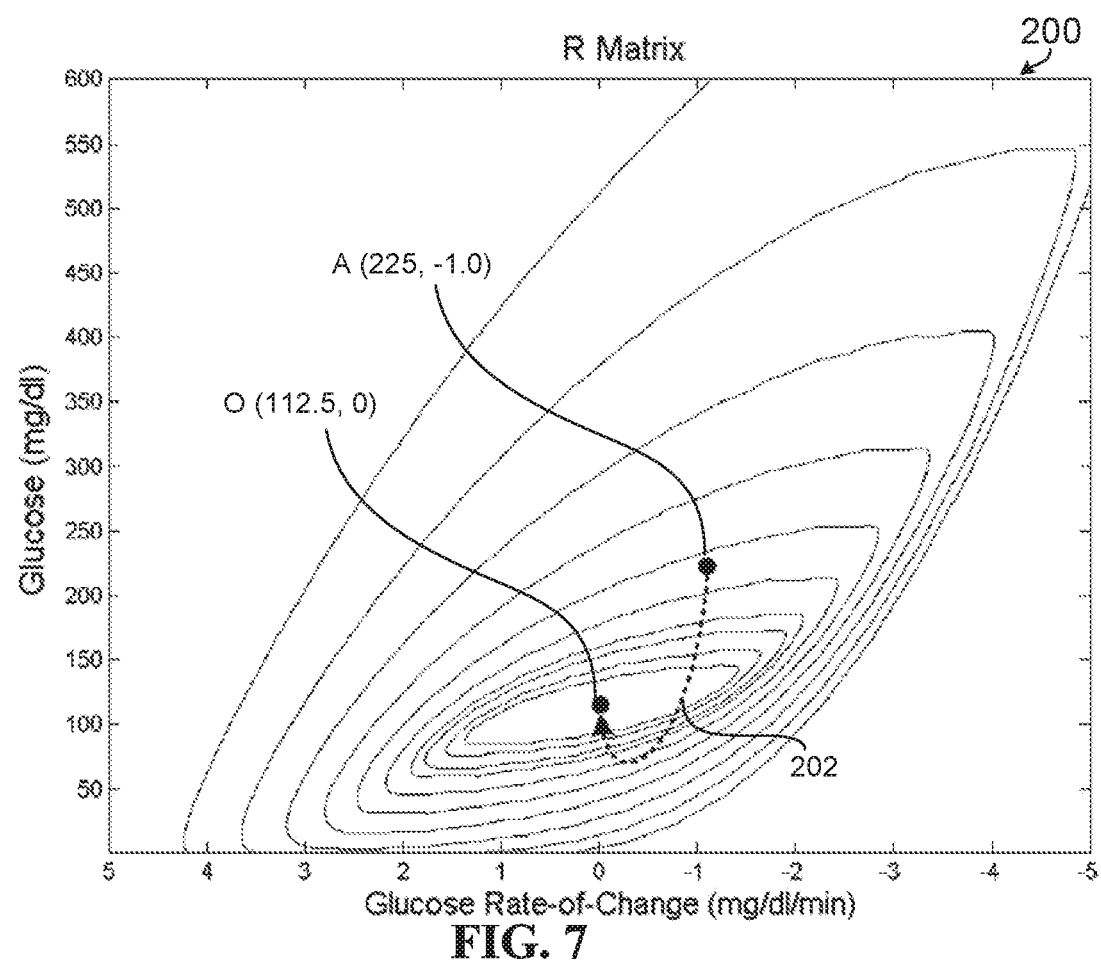
FIG. 7 is a surface graph illustrating exemplary cumulative penalty values for a set of glucose states as calculated by the method of FIGS. 4 and 5.
Figure 8:
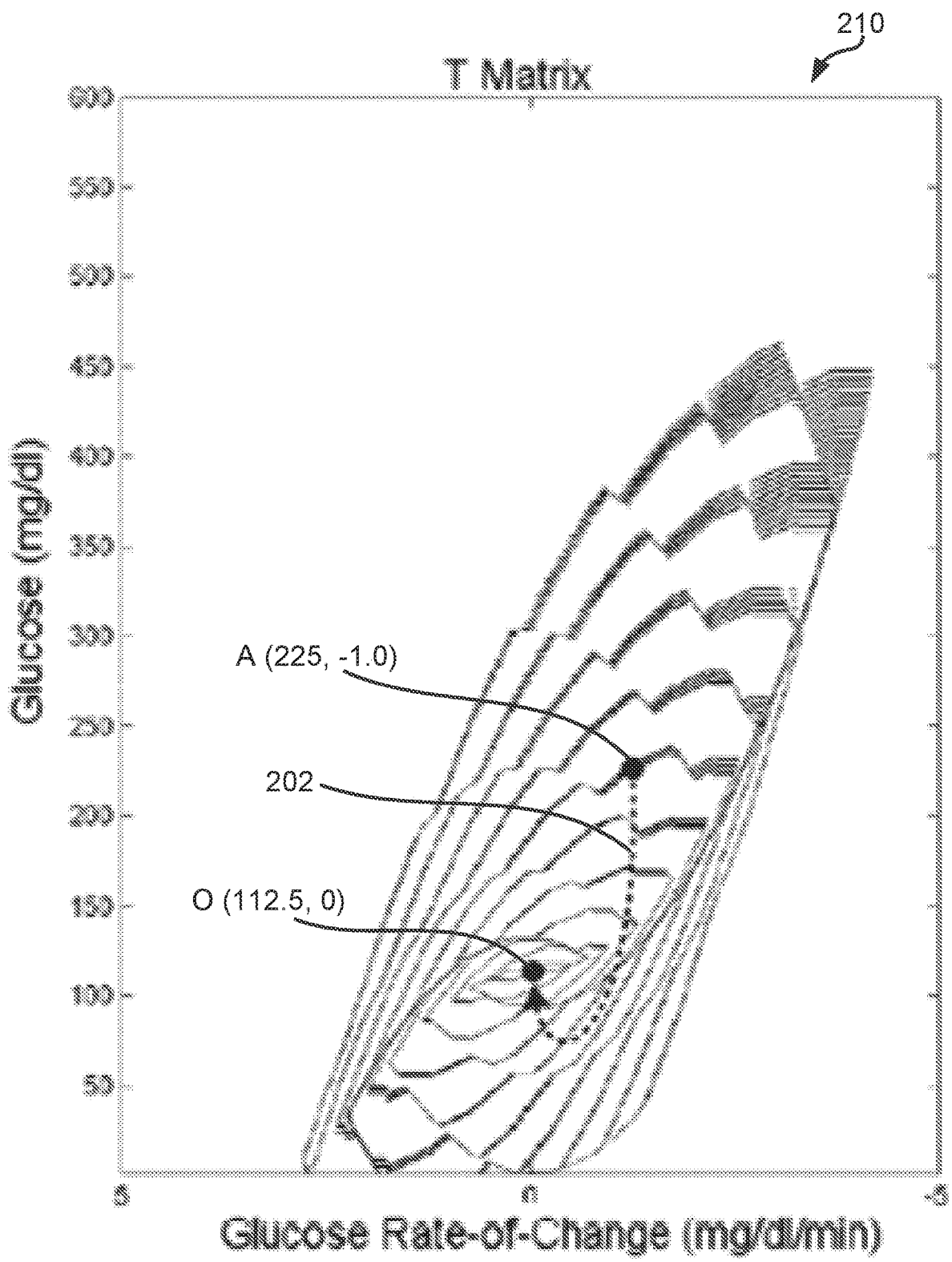
FIG. 8 is a surface graph illustrating exemplary total return times to a target glucose state from a set of glucose states as calculated by the method of FIGS. 4 and 5.
Figure 9:
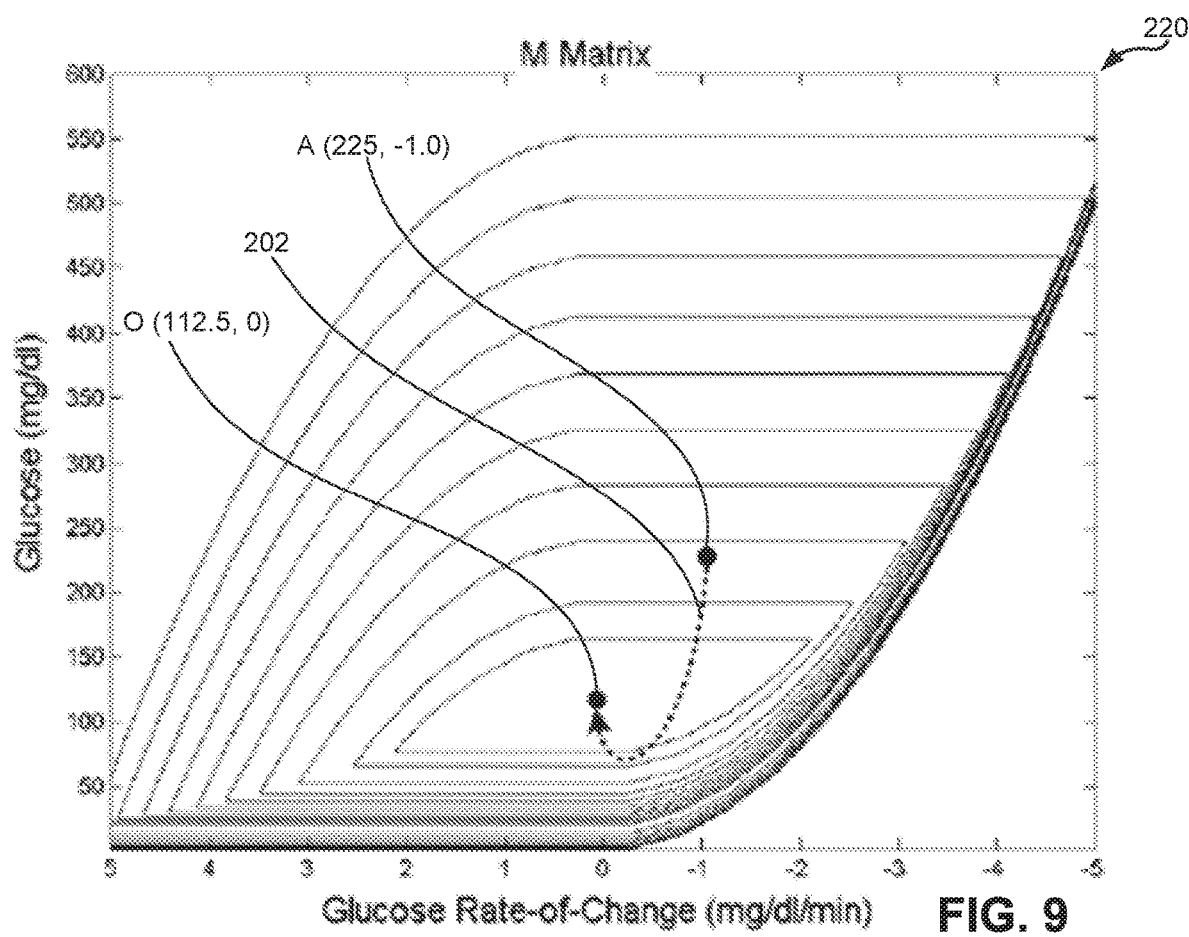
FIG. 9 is a surface graph illustrating exemplary maximum penalty values for a set of glucose states as calculated by the method of FIGS. 4 and 5.
Figure 10:
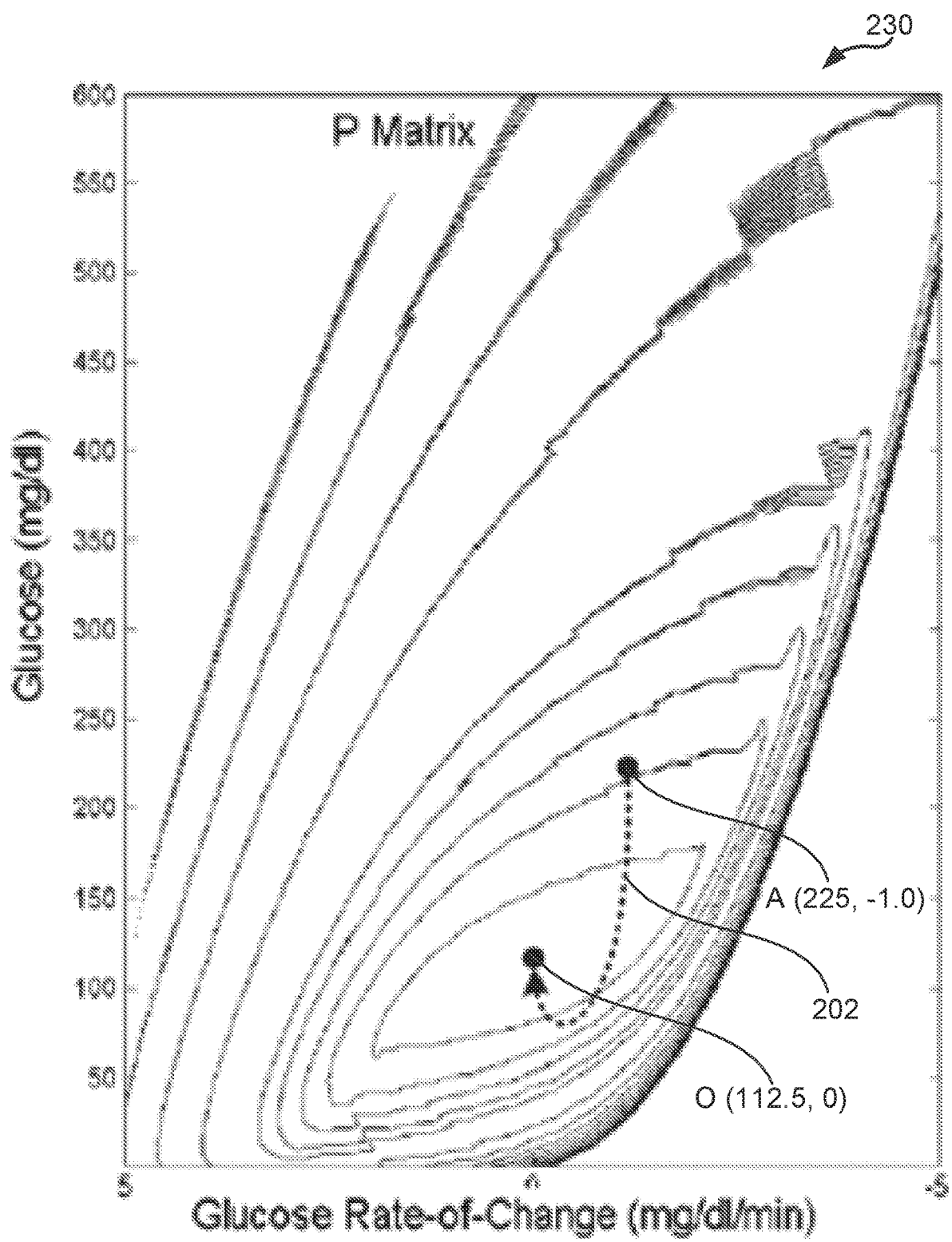
FIG. 10 is a surface graph illustrating exemplary mean penalty rates for a set of glucose states as calculated by the method of FIGS. 4 and 5.

In one embodiment, the calculated matrices R, T, M, and P are used to create surface graphs or contour plots that illustrate the associated risk or hazard metric values of the corresponding matrices R, T, M, and P. See, for example, the exemplary surface contour plots illustrated in FIGS. 7-11 wherein the surface illustrates the corresponding risk or hazard metric value. Surface contour plots of FIGS. 7-11 are generated by the method of FIGS. 4 and 5 based on static penalty values provided with the Kovatchev function (see block 122 of FIG. 4 described herein). While the surface graphs of FIGS. 7-11 are illustratively contour plots, colored surface graphs may also be generated wherein the color/shading of the surface illustrates the corresponding metric value. Referring to FIG. 7, a cumulative penalty surface 200 illustrates the cumulative penalty values calculated by logic 80 for the glucose states of matrix R. The y-axis represents the blood glucose level ranging from 0 mg/dl to 600 mg/dl and the x-axis represents the glucose rate of change ranging from −5 mg/dl/min to 5 mg/dl/min. While matrix R is described above as having a glucose level range of 0 to 400 mg/dl, the surface graphs of FIGS. 7-12 have a glucose level range of 0 to 600 mg/dl for illustrative purposes. An exemplary glucose state is illustrated at point A with a glucose level of 225 mg/dl and a glucose rate of change of −1.0 mg/dl/min (see also FIGS. 8-10). A target return path 202 is illustrated from the glucose state at point A to the optimal glucose state at point O. The target return path 202, calculated to minimize the cumulative penalty value by the method of FIGS. 4 and 5, illustrates the intermediate glucose states of the calculated transition from the glucose state at point A to the optimal glucose state at point O. Similarly, FIGS. 8-10 illustrate surface graphs for the other hazard metrics. Referring to FIG. 8, a total return time surface 210 illustrates the total estimated return times calculated by logic 80 for all glucose states of matrix T. Referring to FIG. 9, a maximum penalty surface 220 illustrates the maximum penalty values calculated by logic 80 for all glucose states of matrix M. Referring to FIG. 10, a penalty rate surface 230 illustrates the mean penalty rates calculated by logic 80 for all glucose states of matrix P.

Figure 18:
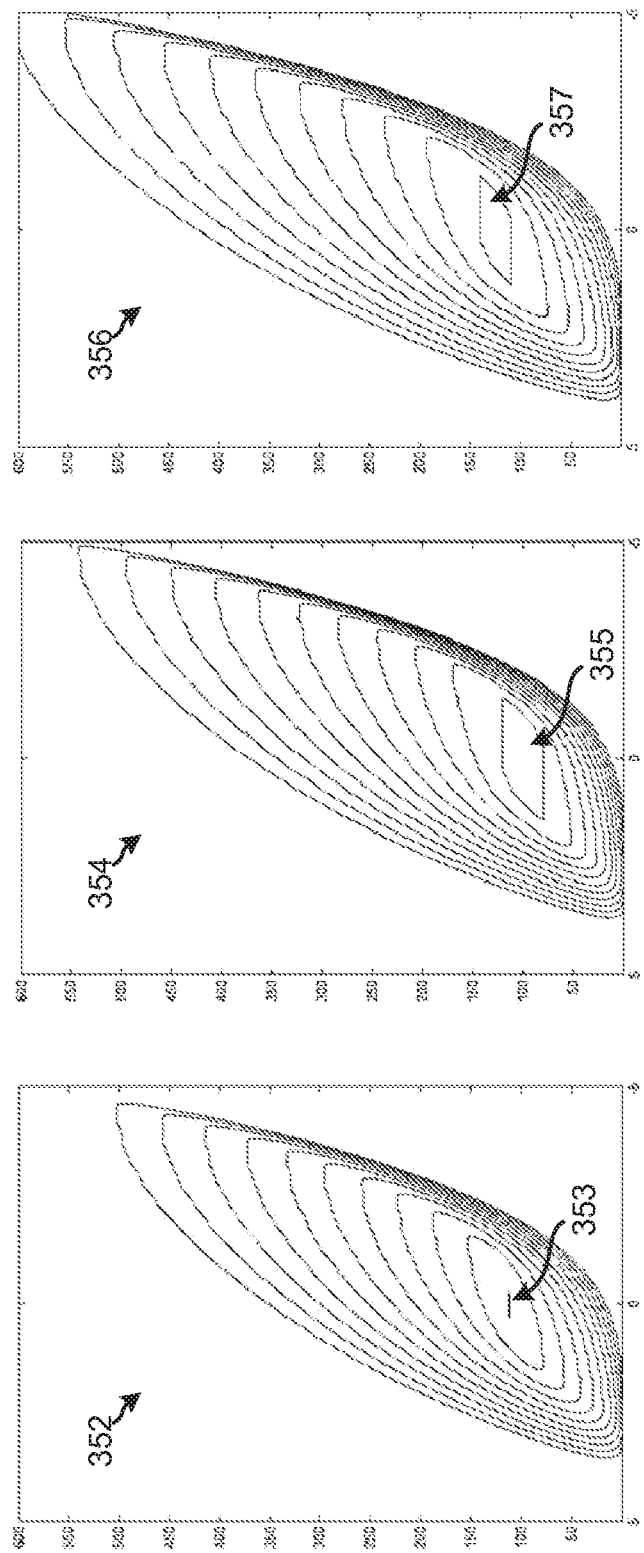
FIG. 18 illustrates three exemplary surface graphs providing exemplary cumulative penalty values for a set of glucose states as calculated by the method of FIGS. 4 and 5 based on the hazard function of FIG. 1A.

Additional surface contour plots are illustrated in FIG. 18 each corresponding to a different cumulative penalty matrix R generated by the method of FIGS. 4 and 5. The plots of FIG. 18 are generated based on static penalty values provided with hazard function 30 (see block 122 of FIG. 4 described herein). As such, the plots of FIG. 18 illustrate different cumulative penalty surfaces 352, 354, 356 for different exemplary ranges of target glucose levels (i.e., $g_1$, $g_2$ values). The y-axis of each surface 352, 354, 356 represents the blood glucose level ranging from 0 mg/dl to 600 mg/dl, and the x-axis represents the glucose rate of change ranging from −5 mg/dl/min to 5 mg/dl/min. Referring to FIG. 18, cumulative penalty surface 352 illustrates the cumulative penalty values for glucose states that are based on a target glucose value of $g_1=g_2=112.5$ mg/dl, with region 353 having the minimal (e.g., zero) cumulative penalty. Cumulative penalty surface 354 illustrates the cumulative penalty values based on a target glucose range of $g_1=80$ mg/dl to $g_2=120$ mg/dl, with region 355 having the minimal (e.g., zero) cumulative penalty. Cumulative penalty surface 356 illustrates the cumulative penalty values based on a target glucose range of $g_1=110$ mg/dl to $g_2=140$ mg/dl, with region 357 having the minimal (e.g., zero) cumulative penalty. Other suitable target glucose ranges may be provided.

Figure 11:
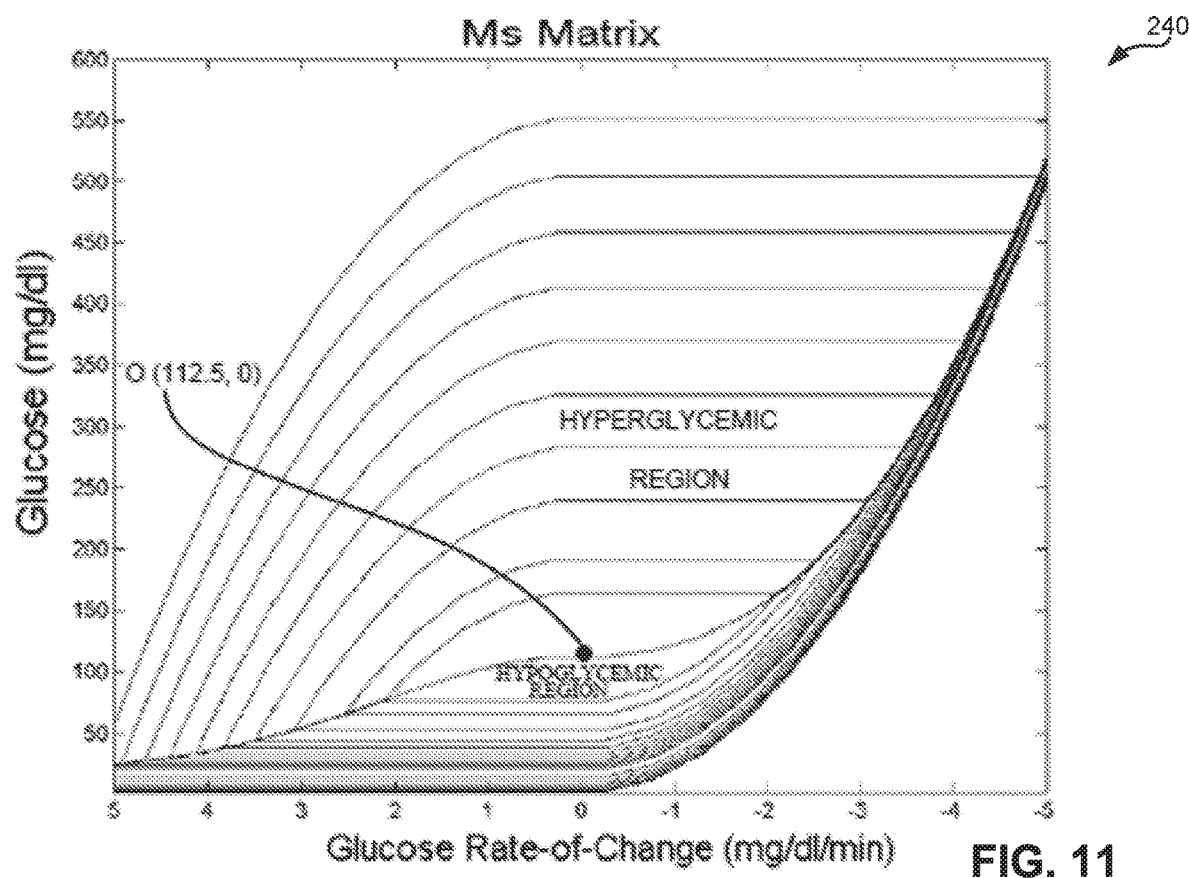
FIG. 11 is a surface graph illustrating exemplary signed maximum penalty values for a set of glucose states as calculated by the method of FIGS. 4 and 5.

Logic 80 is further operative to calculate signed risk/hazard metrics for matrices R, M, P, and B based on the method of FIGS. 4 and 5. In one embodiment, to calculate signed metrics, logic 80 sets the static penalty values associated with hypoglycemic glucose states, i.e., glucose states having a glucose level of less than 112.5 mg/dl, to be negative based on the following equation:

$$H_s(g)=[1.509(\log(g)^{1.0804}-5.381)]^2 * \text{sign}[1.509(\log(g)^{1.0804}-5.381)] \quad (4)$$

wherein g is the glucose level and $H_s(g)$ is the signed static penalty value associated with the glucose level g. Logic 80 calculates the target return path according to the method of FIGS. 4 and 5 by analyzing the absolute value of the signed cumulative penalties. For example, at block 122 of FIG. 4, logic 80 determines if the absolute value of the cumulative penalty value associated with $GS_N$ is greater than the absolute value of the sum of the cumulative penalty value of $GS_Q$ and the static penalty value of $GS_N$. Similarly, at block 148 of FIG. 5, logic 80 determines if the absolute value of the static penalty value of $GS_N$ is greater than the absolute value of the current maximum static penalty value associated with the target return path for $GS_N$. Based on the signed penalty values, logic 80 is operative to generate signed risk surfaces for each matrix R, M, and P. For example, FIG. 11 illustrates a signed maximum penalty surface 240 that distinguishes (e.g., illustratively based on color/shading) between the negative maximum penalties associated with the hypoglycemic region and the positive maximum penalty values associated with the hyperglycemic region.

Computing device 66 of FIG. 3 is further operative to estimate a glucose state of a person based on the measured glucose results provided with glucose sensor 56. In particular, glucose sensor 56 may not function normally due to a malfunction and/or noise associated with glucose sensor 56, potentially resulting in inaccurate glucose measurements. As such, hazard analysis logic 80 of computing device 66 is further operative to analyze the probability of accuracy of the detected glucose state provided with glucose sensor 56. Logic 80 may use any suitable probability analysis tool to determine the probability of accuracy of a measured glucose result, such as a hidden Markov model. Based on the determined probability of accuracy, hazard analysis logic 80 estimates the glucose level and the glucose rate of change of the person using a recursive filter 82 (FIG. 3). In particular, recursive filter 82, such as a Kalman filter, for example, weights the detected glucose state, including the glucose level and rate of change, with the determined probability of glucose sensor accuracy. Further, based on the probability of glucose sensor accuracy, the recursive filter 82 is operative to calculate an uncertainty measure of the estimated glucose state. The uncertainty measure is indicative of the quality of the estimated glucose state. For a series of detected glucose states, the uncertainty for each state may vary. For further description of the probability analysis tool, the recursive filter, the uncertainty calculation, and other probability and risk analysis functionalities of computing device 66, see U.S. patent application Ser. No. 12/693,701, filed on Jan. 26, 2010, entitled "Methods and Systems for Processing Glucose Data Measured from a Person Having Diabetes," the entire disclosure of which is incorporated by reference herein.

Figure 12:
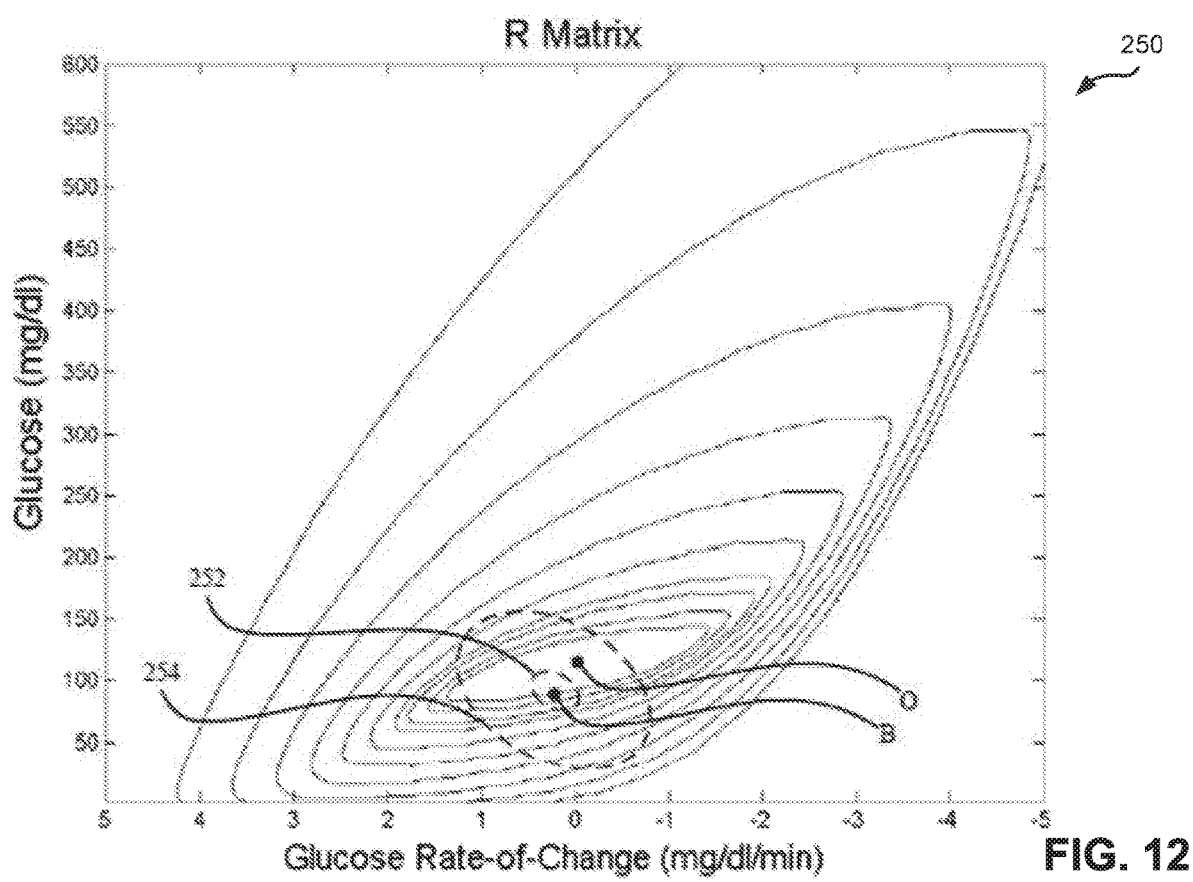
FIG. 12 is a surface graph illustrating exemplary cumulative penalty values for a set of glucose states and an exemplary probability distribution associated with a glucose state.

Referring to FIG. 12, a cumulative penalty surface 250 illustrates the cumulative penalty values calculated by logic 80 for the glucose states of matrix R, as described herein. Upon detection of a glucose state having the glucose level and glucose rate of change corresponding to point B of FIG. 12, logic 80 is operative to calculate the probability distribution around the detected glucose state. FIG. 12 illustrates two alternative distributions 252 and 254. The smaller distribution 252 indicates less uncertainty associated with the detected glucose state, while the larger distribution 254 indicates more uncertainty. Distributions 252 and 254 are illustratively Gaussian (normal) distributions, although other suitable methods of representing uncertainty may be provided, such as a particle filter or a mixture of Gaussians, for example.

Based on the uncertainty associated with a detected glucose state, hazard analysis logic 80 is operative to calculate a risk value for that detected glucose state. In particular, the risk value is equal to the cumulative penalty of the detected glucose state, as provided with matrix R, multiplied by the probability of accuracy of the measured glucose results as determined by logic 80. For a given cumulative penalty of a detected glucose state, the risk value calculated by logic 80 increases with increasing uncertainty of the detected glucose state. For example, distribution 252 of FIG. 12 has smaller risk value than distribution 254 based on the uncertainty being less for distribution 252. In the illustrated embodiment, the calculated risk value may be displayed on display 68 of computing device 66. Further, the calculated risk value may be used to adjust therapy provided to the person with diabetes, such as adjusting an insulin bolus or basal rate, for example. For further description of the risk calculation functionality of computing device 66 as well as the probability distribution calculations, see U.S. patent application Ser. No. 12/818,795, filed on Jun. 18, 2010, entitled "Insulin Optimization Systems and Testing Methods with Adjusted Exit Criterion Accounting for System Noise Associated with Biomarkers," the entire disclosure of which is incorporated by reference herein.

Figure 13:
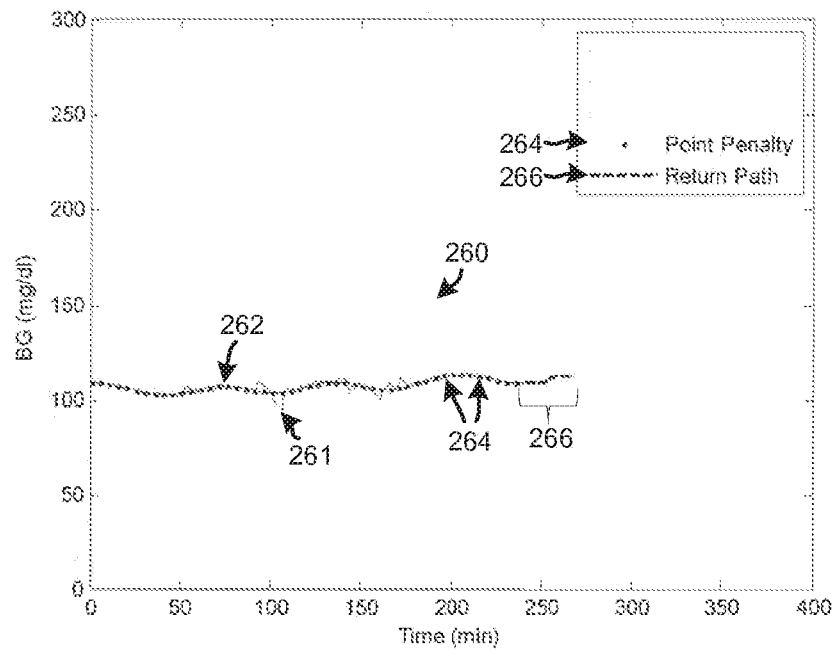
FIG. 13 illustrates an exemplary CGM trace having low cumulative penalty values for glucose states of the CGM trace.
Figure 14:
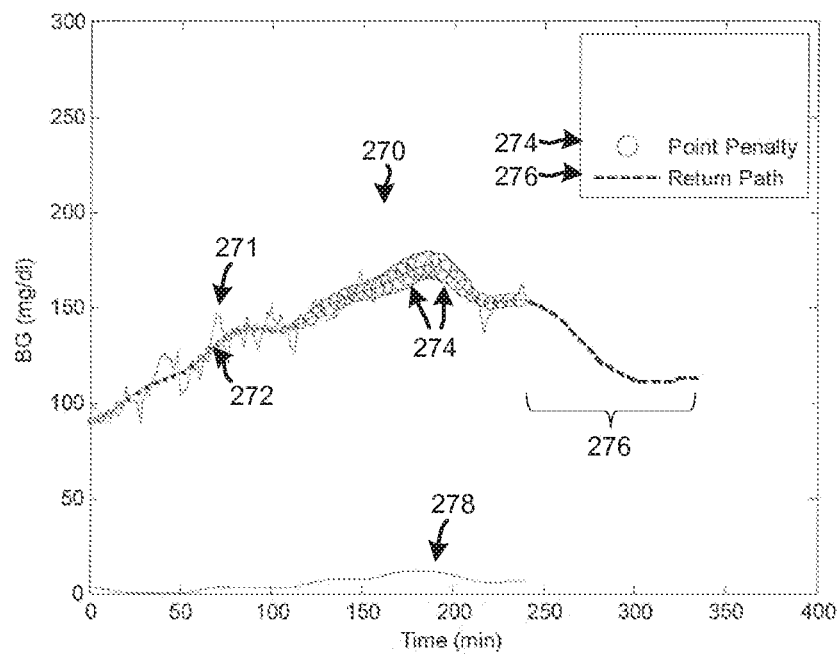
FIG. 14 illustrates another exemplary CGM trace having moderate cumulative penalty values for glucose states of the CGM trace.
Figure 15:
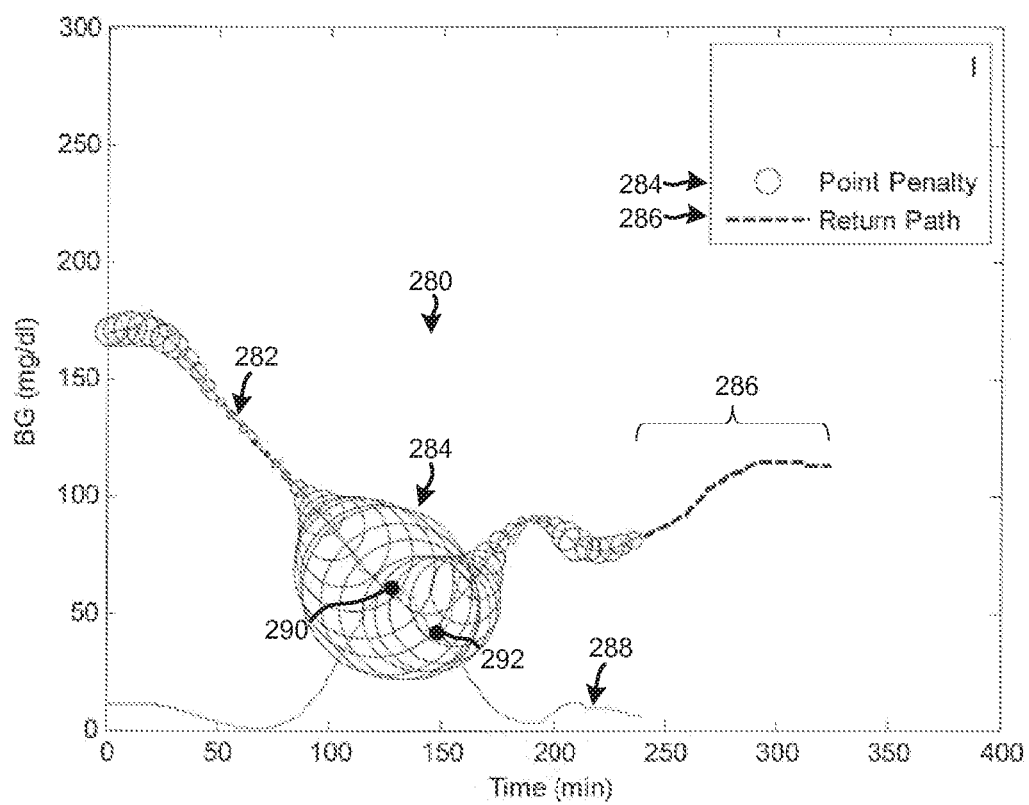
FIG. 15 illustrates another exemplary CGM trace having large cumulative penalty values for glucose states of the CGM trace.

Referring to FIGS. 13-15, several graphs 260, 270, 280 are illustrated each depicting an exemplary CGM trace, wherein the x-axis represents time in minutes and the y-axis represents a blood glucose level in mg/dl. Each CGM trace comprises a series of detected glucose levels measured over a period, thereby illustrating the dynamics of the glucose levels over time. In FIG. 13, exemplary graph 260 is shown including a raw (unfiltered) trace 261 and a filtered glucose trace 262 (i.e., the glucose levels of trace 262 are estimated based on probability of sensor accuracy). Each estimated glucose level of trace 262 includes a corresponding point penalty 264 whose size (diameter) represents the associated cumulative penalty of the glucose level. As illustrated in FIG. 13, the trace 262 stays substantially centered around 110 mg/dl (near the optimal glucose level) with a minimal rate of change, and thus each estimated glucose level has a low cumulative penalty. Also illustrated in FIG. 13 is a target return path 266 that illustrates the intermediate glucose levels over a target return to the optimal glucose level of 112.5 mg/dl, as calculated by logic 80 and described herein. The target return path 266 starts at the final estimated glucose value of trace 262, illustratively at around a time of 240 minutes.

In FIG. 14, exemplary graph 270 illustrates a raw unfiltered trace 271 and a filtered (estimated) glucose trace 272, and each estimated glucose value of trace 272 includes a corresponding point penalty 274 whose size represents the cumulative penalty of the associated glucose level. As illustrated, the trace 272 increases towards hyperglycemia, but the rate of change of the glucose levels of the trace 272 is slow to moderate. As such, point penalties 274 increase in size as the estimated glucose levels increase, but the point penalties 274 are moderately sized. The cumulative penalty values are also illustrated with line 278, which shows that the cumulative penalty maxes out just before the high peak glucose level is reached with the glucose level rising with a positive rate-of-change. Also illustrated in FIG. 14 is a target return path 276 for the final estimated glucose level of trace 272, as calculated by logic 80 and described herein. As shown, the target return path 276 has a longer estimated return time than the target return path 266 of FIG. 13.

In FIG. 15, exemplary graph 280 illustrates a filtered (estimated) glucose trace 282, and each estimated glucose value of trace 282 includes a corresponding point penalty 284 whose size represents the cumulative penalty of the associated glucose level. As illustrated, the trace 282 decreases towards hypoglycemia, and the rate of change of the glucose levels is faster than the rate of change of trace 272 of FIG. 14. As such, point penalties 284 increase in size as the glucose levels rapidly decrease, and the point penalties 284 become relatively large. The cumulative penalties are also illustrated with line 288, showing that the cumulative penalty maxes out (peak 290) before the lowest glucose level (point 292) when the rate-of-change is still falling. As such, the max cumulative penalty at peak 290 illustrates the anticipation of future low glucose levels, and thus future risk, due to the rapidly falling glucose level (identified with the detected rate-of-change). Also illustrated in FIG. 15 is a target return path 286 for the final estimated glucose level of trace 282, as calculated by logic 80 and described herein.

A total penalty value J for a CGM trace may also be calculated with logic 80 based on the following equation:

$$J(g_{1...\tau}, dg_{1...\tau}) = \sum_{i=1}^{\tau} f_1(g_i, dg_i) + \mu f_2(g_\tau, dg_\tau) \quad (5)$$

wherein $f_1$ is the cumulative penalty of a given glucose state of the trace, $f_2$ is the cumulative penalty of the final glucose state of the trace, g is the glucose level, dg is the glucose rate of change, and $\mu$ is a parameter used to tune the balance between the cumulative penalty of the trace and the cumulative penalty of the final state. As such, the total penalty J of a CGM trace is the sum of the cumulative penalty for each point in the trace plus the cumulative penalty for the final state. Alternatively, $f_1$ and $f_2$ may be another penalty function described herein, such as the mean penalty rate or maximum cumulative penalty, or a combination of the penalty functions described herein.

Figure 16:
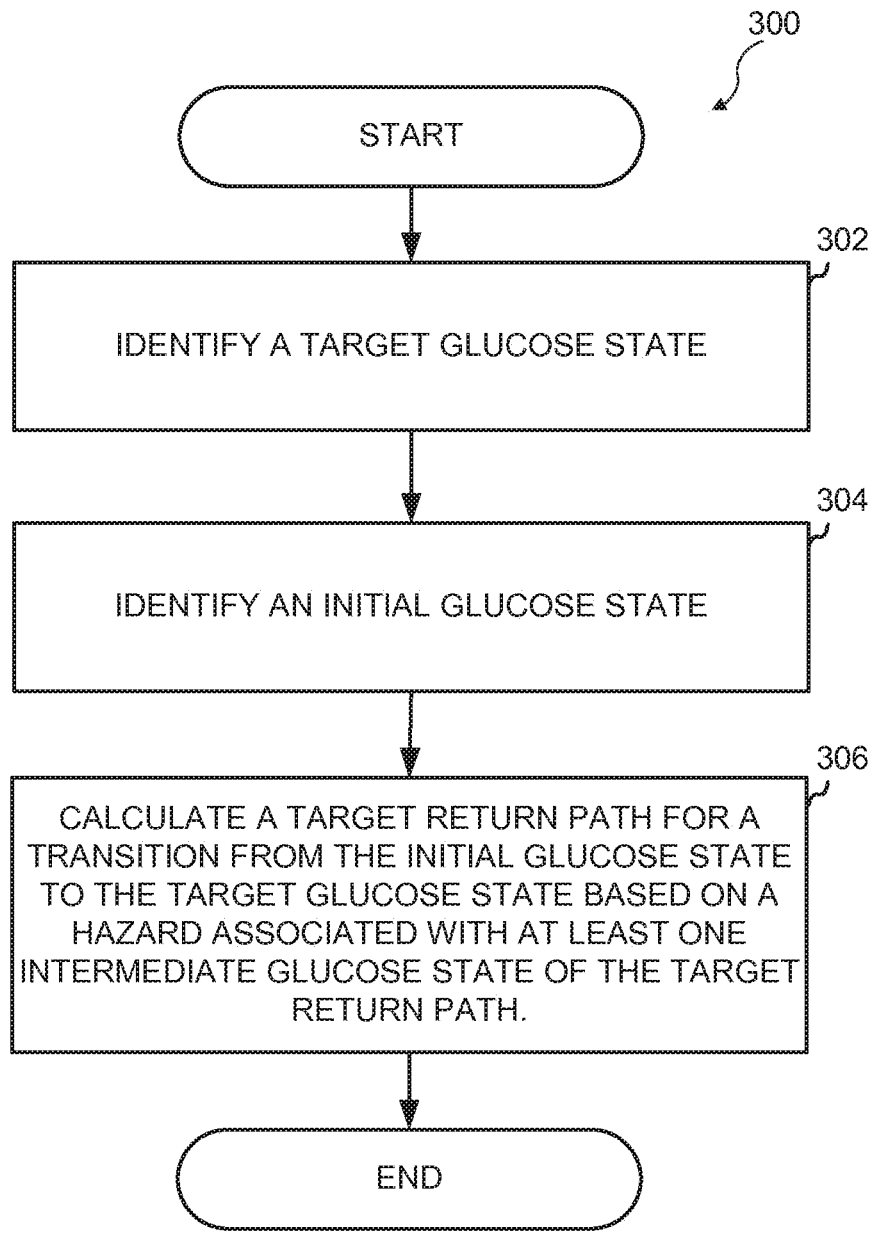
FIG. 16 illustrates a flow chart of another exemplary method of operation of the computing device of FIG. 3 for calculating a target return path from an initial glucose state to a target glucose state.

Referring to FIG. 16, a flow diagram 300 of an exemplary method performed by hazard analysis logic 80 of FIG. 3 is illustrated for calculating a target return path from an initial glucose state to a target glucose state. Reference is made to the method of FIGS. 4 and 5 throughout the description of FIG. 16. At block 302, logic 80 identifies a target glucose state including a target glucose level and a target rate of change of the target glucose level. In one embodiment, the target glucose level is the optimal glucose level identified in the method of FIGS. 4 and 5 and described herein having an associated penalty/risk value of zero. At block 304, logic 80 identifies an initial glucose state including an initial glucose level and an initial rate of change of the initial glucose level. The initial glucose state is different from the target glucose state. In one embodiment, the initial glucose state is a next glucose state $GS_N$ evaluated in the method of FIGS. 4 and 5. In another embodiment, the initial glucose state is a detected glucose state based on measured glucose results from glucose sensor 56 (FIG. 2).

At block 306, logic 80 calculates a target return path for a transition from the initial glucose state to the target glucose state. As described herein, the target return path comprises at least one intermediate glucose state associated with the transition from the initial glucose state to the target glucose state. The target return path is calculated by logic 80 based on a hazard associated with the at least one intermediate glucose state of the target return path, as described herein. In one embodiment, logic 80 identifies a plurality of potential intermediate glucose states between the initial glucose state and the target glucose state and selects the at least one intermediate glucose state from the plurality of potential intermediate glucose states to minimize the hazard associated with the target return path. For example, to find the target return path that has a minimum cumulative penalty, logic 80 in FIGS. 4 and 5 evaluates same next glucose states $GS_N$ multiple times when evaluating different glucose states of interest $GS_Q$ throughout the execution of the method. Logic 80 then assigns each $GS_N$ to a target return path that has the minimum cumulative penalty, as described herein.

In one embodiment, the target return path is calculated at block 306 further based on a physiological limit of a glucose perturbation, such as a predetermined maximum acceleration, as described herein. In one embodiment, logic 80 calculates the target return path at block 306 by identifying a plurality of potential glucose states ($GS_N$) based on the target glucose state, the physiological limit of the glucose perturbation (e.g., the assumed maximum acceleration), and a predetermined period (e.g., the incremented time step of block 108 of FIG. 4), as described herein with respect to FIGS. 4 and 5. For example, the transition to the target glucose state from each of the potential glucose states is assumed by logic 80 to be attainable by a person within the predetermined period based on the physiological limit.

In one embodiment, logic 80 calculates a target return path for a plurality of initial glucose states (e.g., the glucose states of matrix R), and each target return path is calculated by logic 80 to minimize the hazard (i.e., penalty values) associated with intermediate glucose states of the target return path, as described herein. In one embodiment, logic 80 creates one or more lookup tables that store the values of matrices R, T, M, P, and B for each glucose state. The lookup table may be used to analyze various risks or hazards associated with a particular glucose state of interest. For example, upon detecting a glucose state of a person with CGM system 50 (FIG. 2), the calculated matrices R, T, M, P, and B stored in the look-up table (e.g., stored in memory 76 of FIG. 3) may be accessed to identify a risk metric associated with a stored glucose state that is substantially the same as the detected glucose state. In one exemplary embodiment, logic 80 is operative to look up the following from the lookup table: a cumulative penalty value associated with the detected glucose state from matrix R, an estimated return time for the detected glucose state from matrix T, an maximum penalty value associated with a target return path for the detected glucose state from matrix M, and a mean penalty rate associated with the target return path from matrix P. Logic 80 also identifies the optimal or target return path for the detected glucose state based on mapping provided with the back pointers of matrix B. In one embodiment, logic 80 displays the identified risk metric on display 68 of FIG. 2 or transmits it to a remote computing system.

In one embodiment, logic 80 calculates multiple sets of matrices R, T, M, and P based on different maximum glucose perturbations (defined at block 114 of FIG. 4) to thereby generate a plurality of lookup tables that each corresponds to a different set of matrices R, T, M, and P. For example, logic 80 calculates a different lookup table for each of a plurality of different maximum glucose accelerations defined at block 114 of FIG. 4, and each lookup table thereby contains a unique set of risk or hazard metrics that correspond to the associated maximum glucose acceleration. Each lookup table may then be used for risk or hazard analysis. In one embodiment, computing device 66 selects a lookup table from the group of lookup tables for risk analysis based on at least one user-defined parameter that is input or programmed into CGM system 50 (FIG. 2). For example, a user may enter their age or some other suitable parameter via a user interface of computing device 66. As described above, the age of the person with diabetes may be relevant to the selection of an appropriate maximum glucose acceleration. Based on the entered parameter(s), logic 80 selects a lookup table that corresponds to that parameter (e.g., age) based on the maximum glucose acceleration associated with the selected lookup table. The selected lookup table may then be used to compute risk metrics for a detected glucose state of the person, as described herein.

Figure 17:
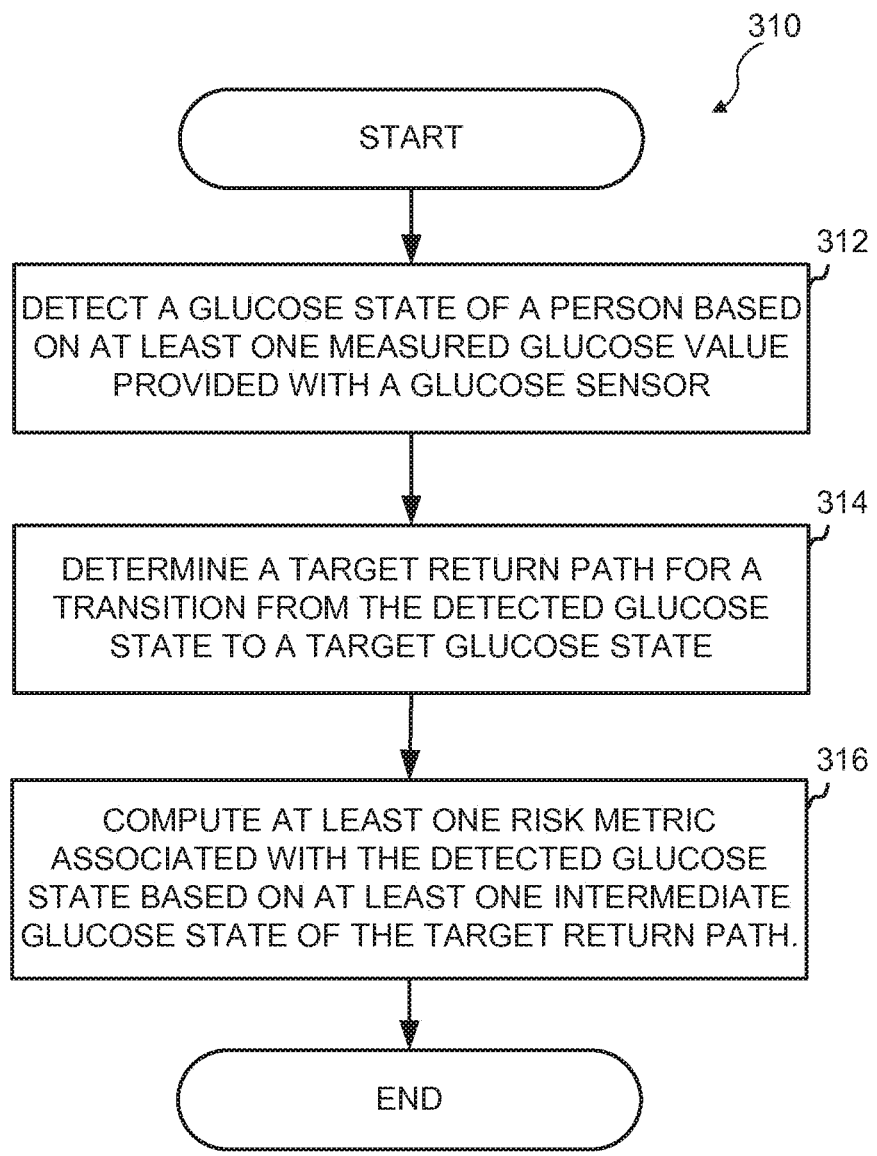
FIG. 17 illustrates a flow chart of another exemplary method of operation of the computing device of FIG. 3 for determining a risk metric associated with a detected glucose state.

Referring to FIG. 17, a flow diagram 310 of another exemplary method performed by hazard analysis logic 80 of FIG. 3 is illustrated for assessing risk associated with a detected glucose state. At block 312, logic 80 detects a glucose state of a person based on at least one measured glucose value provided with glucose sensor 56, as described herein. At block 314, logic 80 determines a target return path for a transition from the detected glucose state to a target glucose state, as described herein. In one embodiment, logic 80 determines the target return path at block 314 by identifying the glucose state in the lookup table that is nearest to the detected glucose state. The target return path associated with the identified nearest glucose state of the lookup table is then identified as the target return path for the detected glucose state. At block 316, logic 80 computes at least one risk metric associated with the detected glucose state based on at least one intermediate glucose state of the target return path. In one embodiment, the at least one risk metric is computed by looking up the risk metric associated with the detected glucose state from the lookup table stored at memory 76 and described above. For example, the risk metric may include a cumulative penalty value, a total estimated time to return to the target glucose state from the detected glucose state, a mean penalty rate associated with the target return path, and a maximum penalty value associated with the target return path. In one embodiment the at least one risk metric is a cumulative risk value calculated by logic 80, as described below.

In particular, the lookup table is further used to consider the uncertainty of a detected glucose state when analyzing the risk associated with the detected glucose state. In one embodiment, logic 80 calculates the risk associated with the detected glucose state and with all other glucose states of matrix R of the lookup table. Logic 80 then sums all of these individual risk values to determine a cumulative risk (at block 316) associated with the detected glucose state. For example, upon detecting a glucose state of a person at block 312, logic 80 calculates the probability that the person is in that detected glucose state, as described above. Logic 80 further calculates the probability that the person is in each of the other glucose states of the penalty matrix R, such as based on the probability distribution of the detected glucose state described above. In one embodiment, calculating the probability of each glucose state includes calculating the probability or uncertainty of the glucose level and the probability or uncertainty of the glucose rate of change for each glucose state. Based on the probability calculations, logic 80 then calculates the risk associated with each glucose state of matrix R, including the detected glucose state. As described above, each risk value is computed based on the product of the probability measure and the corresponding cumulative penalty value of the glucose state. Finally, logic 80 sums all of the computed risks of the glucose states of matrix R to determine a total or cumulative risk associated with the detected glucose state. The cumulative risk value may be stored in memory 76 (FIG. 3), may be presented to a user on display 68 (FIG. 3), and/or may be used for additional analyses or control strategies.

Alternatively, logic 80 may calculate the probability and associated risk for each of a subset of glucose states of matrix R (e.g., glucose states that are near the detected glucose state or are within a certain range of the probability distribution) rather than all glucose states of the matrix R. Further, the cumulative risk calculation may be calculated for other risk metrics, such as the risk metrics provided in the other penalty matrices described herein (E.g., matrix M, P, or T).

Based on a determined target return path for a detected glucose state of a person, various control strategies may be employed either by computing device 66, by another system, or by human intervention. For example, computing device 66 may be in communication with a treatment system, such as an insulin therapy system or device. Based on the target return path and/or risk metric identified for the detected glucose state, computing device 66 is operative to adjust, for example, a basal rate and/or bolus of an insulin treatment or another appropriate treatment to the person. For example, the insulin treatment may be adjusted such that the person's return towards the target glucose state substantially follows the target return path.

The risk metric values associated with the target return path for a detected glucose state may be undesirable or may exceed predefined limits, and thus treatment is adjusted such that a different return path towards the target glucose state is followed. For example, it may be desirable to avoid a maximum penalty value that is identified with the target return path for the detected glucose state due to the increased hazard or risk to the person that is associated with that penalty value. For example, the maximum penalty value may exceed a predetermined risk threshold identified for the person. As such, treatment may be adjusted such that the glucose state where the maximum penalty value occurs is avoided during the person's return towards the target glucose state. In this example, the therapy may be adjusted such that it follows a second return path that avoids the glucose state having the maximum penalty value.

Risk metrics for a glucose trace may be used retrospectively to analyze and draw inferences from behaviors of the person with diabetes and to identify and target areas of focus for the diabetes management. Behaviors may include meals, boluses, basal rates, exercise, hypo/hyper interventions, correction boluses, sleep, etc. Risk metrics such as the cumulative penalty and the mean penalty rate may be used to associate behaviors of the person with diabetes to an increase in the cumulative penalty or mean penalty rate to thereby identify behaviors that tend to result in increased levels of risk.

While various embodiments of devices, systems, methods, and non-transitory computer readable medium for analyzing a glucose state have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

What is claimed is:

1. A method of analyzing a glucose state, the method comprising:
   identifying, by at least one computing device, a target glucose state including a target glucose level and a target rate of change of the target glucose level;
   identifying, by the at least one computing device, an initial glucose state including an initial glucose level and an initial rate of change of the initial glucose level, the initial glucose state being different from the target glucose state;
   calculating, by hazard analysis logic of the at least one computing device, a target return path for a transition from the initial glucose state to the target glucose state, the target return path comprising at least one intermediate glucose state associated with the transition from the initial glucose state to the target glucose state, the target return path being calculated by the hazard analysis logic based on a hazard associated with the at least one intermediate glucose state of the target return path;
   adjusting, by the at least one computing device, a therapy to transition from the identified initial glucose state towards the identified target glucose state based on the target return path;
   calculating, by the at least one computing device, a total estimated time for a transition from the identified initial glucose state to the identified target glucose state along the target return path, the calculation based on a predetermined maximum acceleration of glucose, wherein the predetermined maximum acceleration of glucose includes a positive value and a negative value of acceleration.

2. The method of claim 1, wherein the calculating comprises:
   identifying a plurality of potential intermediate glucose states between the initial glucose state and the target glucose state, and
   selecting the at least one intermediate glucose state from the plurality of potential intermediate glucose states for the target return path to minimize the hazard associated with the target return path.

3. The method of claim 2, wherein the at least one intermediate glucose state of the target return path comprises a plurality of intermediate glucose states each having an associated penalty value, the plurality of intermediate glucose states are selected from the plurality of potential intermediate glucose states to minimize a sum of the penalty values associated with the target return path, and each penalty value includes a measure of the hazard associated with the corresponding intermediate glucose state.

4. The method of claim 1, wherein the target return path is calculated by the at least one computing device further based on a physiological limit of a glucose perturbation.

5. The method of claim 4, wherein the physiological limit comprises a predetermined maximum acceleration of a glucose level.

6. The method of claim 4, wherein the calculating comprises:
   identifying a plurality of potential glucose states based on the target glucose state, the physiological limit of the glucose perturbation, and a predetermined period for a transition from each of the plurality of potential glucose states to the target glucose state, and
   selecting an intermediate glucose state from the plurality of potential glucose states for the target return path to minimize the hazard associated with the target return path.

7. The method of claim 1, further comprising:
   generating, by the hazard analysis logic, a lookup table that maps each of a plurality of initial glucose states to a corresponding target return path, and
   storing the lookup table in memory accessible by the at least one computing device.

8. The method of claim 7, further comprising:
   detecting a glucose state of a person with diabetes based on at least one measure glucose value provided with a glucose sensor;
   accessing, by the hazard analysis logic, the lookup table to identify the initial glucose state from the plurality of initial glucose states that is substantially the same as the detected glucose state of the person; and
   identifying a penalty value in the lookup table associated with the identified initial glucose state, the penalty value representing a hazard associated with the identified initial glucose state based on the corresponding target return path of the identified initial glucose state.

9. The method of claim 8, wherein the detected glucose state includes a glucose level, a rate of change of the glucose level, and an uncertainty of at least one of the glucose level and the rate of change, the method further comprising calculating a risk associated with the detected glucose state based on the penalty value and the uncertainty.

10. The method of claim 8, further comprising providing the penalty value for display on a display.

11. The method of claim 1, wherein the target glucose state is an optimal glucose state having a penalty value of zero, wherein the penalty value represents a hazard associated with the target glucose state.

12. The method of claim 1, wherein the target glucose state includes a target glucose level of about 112.5 milligrams per deciliter and a target rate of change of about zero milligrams per deciliter per second.

13. A non-transitory computer-readable medium comprising:
executable instructions such that when executed by at least one processor cause the at least one processor to:
identify a target glucose state including a target glucose level and a target rate of change of the target glucose level;
identify an initial glucose state including an initial glucose level and an initial rate of change of the initial glucose level, the initial glucose state being different from the target glucose state;
calculate a target return path for a transition from the initial glucose state to the target glucose state, the target return path comprising at least one intermediate glucose state associated with the transition from the initial glucose state to the target glucose state, the target return path being calculated by the at least one processor based on a hazard associated with the at least one intermediate glucose state of the target return path;
adjust a therapy to transition from the identified initial glucose state towards the identified target glucose state based on the target return path;
calculate a total estimated time for transition from the identified initial glucose state to the target glucose state along the target return path using a predetermined maximum acceleration of glucose, wherein the predetermined maximum acceleration includes a positive value and a negative value of acceleration, and wherein the total estimated time is further calculated based on a plurality of acceleration values between the positive value and the negative value.

14. The non-transitory computer-readable medium of claim 13, wherein the executable instructions further cause the at least one processor to:
identify a plurality of potential intermediate glucose states between the initial glucose state and the target glucose state; and
select the at least one intermediate glucose state from the plurality of potential intermediate glucose states for the target return path to minimize the hazard associated with the target return path.

15. The non-transitory computer-readable medium of claim 14, wherein the at least one intermediate glucose state of the target return path comprises a plurality of intermediate glucose states each having an associated penalty value, the plurality of intermediate glucose states are selected by the at least one processor from the plurality of potential intermediate glucose states to minimize a sum of the penalty values associated with the target return path, and each penalty value includes a measure of the hazard associated with the corresponding intermediate glucose state.

16. The non-transitory computer-readable medium of claim 13, wherein the target return path is calculated by the at least one processor further based on a physiological limit of a glucose perturbation.

17. The non-transitory computer-readable medium of claim 16, wherein the executable instructions further cause the at least one processor to:
identify a plurality of potential glucose states based on the target glucose state, the physiological limit of the glucose perturbation, and a predetermined period for a transition to the target glucose state from each of the potential glucose states; and
select an intermediate glucose state from the plurality of potential glucose states for the target return path to minimize the hazard associated with the target return path.

18. The non-transitory computer-readable medium of claim 13, wherein the executable instructions further cause the at least one processor to:
generate a lookup table that maps each of a plurality of initial glucose states to a corresponding target return path, and
store the lookup table in memory accessible by the at least one processor.

19. The non-transitory computer-readable medium of claim 18, wherein the executable instructions further cause the at least one processor to:
detect a glucose state of a person with diabetes based on at least one measured glucose value provided with a glucose sensor;
access the lookup table to identify the initial glucose state from the plurality of initial glucose states that is substantially the same as the detected glucose state of the person; and
identify a penalty value in the lookup table associated with the identified initial glucose state, the penalty value representing a hazard associated with the identified initial glucose state based on the corresponding target return path of the identified initial glucose state.

* * * * *